US011134828B2

United States Patent
Accattato

(10) Patent No.: US 11,134,828 B2
(45) Date of Patent: Oct. 5, 2021

(54) PORTABLE DEVICE FOR CLEANING AND/OR SANITIZING JEWELRY AND OTHER SMALL PARTS

(71) Applicant: JEWELRY SPA HOT TUB INC., Nyack, NY (US)

(72) Inventor: Carlo Accattato, New York, NY (US)

(73) Assignee: JEWELRY SPA HOT TUB INC., Nyack, NY (US)

( * ) Notice: Subject to any disclaimer, the term of this patent is extended or adjusted under 35 U.S.C. 154(b) by 448 days.

(21) Appl. No.: 16/137,042

(22) Filed: Sep. 20, 2018

(65) Prior Publication Data

US 2020/0094292 A1 Mar. 26, 2020

(51) Int. Cl.
*A47L 25/00* (2006.01)
*B08B 11/00* (2006.01)
*B08B 3/08* (2006.01)

(52) U.S. Cl.
CPC .............. *A47L 25/00* (2013.01); *B08B 11/00* (2013.01); *B08B 3/08* (2013.01)

(58) Field of Classification Search
None
See application file for complete search history.

(56) References Cited

U.S. PATENT DOCUMENTS

| 2,141,713 | A | 12/1938 | Hensler et al. |
| 4,941,490 | A | 7/1990 | Gross |
| 5,209,784 | A | 5/1993 | Bellman |
| 5,876,513 | A | 3/1999 | Frankson |
| 6,076,538 | A | 6/2000 | Frankson |
| 6,129,097 | A | 10/2000 | Papandrea |
| 6,338,350 | B1 | 1/2002 | Ewen |
| 6,719,850 | B2 | 4/2004 | Glucksman et al. |
| 7,257,319 | B1 | 8/2007 | Clarke |
| 7,448,398 | B2 | 11/2008 | Glucksman et al. |
| 9,339,852 | B1 | 5/2016 | Campbell |
| 9,365,809 | B1 | 6/2016 | Maiuri |
| 2004/0040586 | A1 | 3/2004 | Kumar |
| 2005/0159326 | A1 | 7/2005 | Hollingsworth |
| 2010/0186780 | A1 | 7/2010 | Larocca et al. |
| 2013/0306111 | A1 | 11/2013 | Myers |
| 2014/0360535 | A1* | 12/2014 | Andrus .................. A47J 43/24 134/25.3 |

* cited by examiner

*Primary Examiner* — Mikhail Kornakov
*Assistant Examiner* — Ryan L Coleman
(74) *Attorney, Agent, or Firm* — Nolte Lackenbach Siegel; Myron Greenspan

(57) ABSTRACT

A portable cleaning device comprising a generally cylindrical container for receiving a fluid to a predetermined level and defining a container axis and having a bottom wall and a top opening at opposing axial ends along said container axis; a basket for supporting items to be cleaned and dimensioned to be removably receivable within said container, said basket defining a basket axis that is substantially coextensive with said container axis when said basket is received within said container and being configured to be rotatably supported for rotation on said bottom wall about said axes when received within said container; and spinning means for spinning said basket on said bottom wall about said axes when said basket is received within said container, whereby spinning said basket within said container on said bottom wall when immersed in fluid below said predetermined level creates turbulence and agitates the fluid in contact with the items to be cleaned to dislodge soil particles and contaminants from the items to be cleaned.

28 Claims, 23 Drawing Sheets

Fig 9IFig 9J

PORTABLE DEVICE FOR CLEANING AND/OR SANITIZING JEWELRY AND OTHER SMALL PARTS

BACKGROUND OF THE INVENTION

1. Field of the Invention

The present invention generally relates to the field of cleaning parts and, more specifically, to a portable cleaning device that can be used to clean and/or sanitize jewelry and other small parts.

2. Description of the Prior Art

Precious stone and metal jewelry is at its most beautiful when perfectly clean and free from body oils, film, grime, and other deposits that can hide the shine, sparkle and character of the jewelry. Notwithstanding the desirability of maintaining jewelry in a very clean state, it is difficult to effectively clean jewelry.

The professional process of cleaning jewelry involves the following steps. First, the jewelry pieces are boiled in a concentrated cleaning solution for about 15 to 30 minutes. Next, the jewelry is removed from the concentrated cleaning solution and is rinsed with hot water. Lastly, the jewelry is subjected to high pressure steaming to quickly remove any remaining water to prevent spotting. While cleaning in this manner renders a piece of jewelry the benchmark 100% clean, the equipment, time, and steps involved in professionally cleaning jewelry is out of reach of the vast majority of consumers and even small jewelry stores with limited space. As a result, there have been attempts to devise less costly and involved devices and methods for cleaning jewelry. For example, liquid jewelry soaking solutions are available. A user will soak a jewelry piece for some time, and then attempt to brush away the grime. Results of about 30-50% are about the best achievable. Commercial ultrasonic jewelry cleaning machines are now being sold. However, these machines can only accomplish cleaning to about 70-80% clean. Also, most of these machines are bulky, heavy and costly. See U.S. Patent Publication Nos. 2013/0306111 to Myers; 2004/0040586 to Kumar and 2010/0186780 to Larocca et al for a dental appliance cleaning apparatus. See also, U.S. Pat. No. 9,339,852 to Campbell that discloses a cleaning device used to clean jewelry by heating clean water dispensed through jet nozzles to spray the jewelry while in a rotating basket.

U.S. Pat. No. 4,941,490 to Gross discloses a low temperature apparatus for cleaning jewelry. The Gross device delivers a low temperature mist of cleaning liquid and a stream of compressed warm air for drying the jewelry once it is cleaned.

U.S. Pat. No. 5,209,784 to Bellman discloses a method and apparatus for jewelry and small parts cleaning. In the Bellman method and apparatus, a large mesh basket with internal hooks posts and compartments is provided for placement in an automatic dishwasher, where the water and water laced detergent will be allowed to impinge on the jewelry pieces contained in the basket and thereby cause cleaning. According to Bellman, results of 80-85% cleaning of oil and dirt can be achieved using the patented method. While this range of results is comparable or better than that achieved with other available non-professional cleaning methods, it still falls short of the perfect results achieved by professional methods of cleaning, which leaves jewelry most brilliant.

Accordingly, there remains a need for a simple and easy to use method and kit for cleaning and/or sanitizing jewelry which achieves 95%+ cleaning results.

Known jewelry cleaning devices use sonic technologies, pressurized steam and other cleaning chemicals to remove or dissolve foreign substances from jewelry. These devices are largely for personal use.

More recent jewelry cleaning devices and methods are sonic cleaners, described in U.S. Pat. No. 6,719,850 issued to Glucksman et al. on Apr. 13, 2004, and U.S. Pat. No. 7,448,398 issued to Glucksman et al. on Nov. 11, 2008; steam cleaners, described in U.S. Pat. No. 6,129,097 issued to Edward Papandrea on Oct. 10, 2000 and U.S. Pat. No. 7,257,319 issued to Michael Clarke on Aug. 14, 2007; and a method describing a complete immersion in cleaning solution, without vibration, described in U.S. Pat. No. 6,076,538 issued to Jon Frankson on Jun. 20, 2000 and patents by others almost a half-century before that time.

U.S. Pat. No. 6,719,850 discloses a small, quiet, sonic cleaner where jewelry is immersed in a cleaning solution and vibrated in the sonic range. The patent also discloses the method for using the cleaner. The patent discloses hooks within the cleaning tank where jewelry can be fastened which rotate in response to the vibrations. U.S. Pat. No. 7,448,398 discloses an improvement over U.S. Pat. No. 6,719,850 in that it provides for removable tanks for ease of disposal and replacement of spent cleaning solutions. Both of these patents disclose machines that are primarily for in-home use.

U.S. Pat. No. 6,338,350 discloses a device which can be attached to a steam cleaning machine to clean jewelry. The device consists of a nozzle through which a jet of steam enters a closed mesh container that holds the jewelry being cleaned. The attachment is mounted to the steam cleaning machine through a support located at the open top of the neck portion of the attachment. This patent also teaches the use of tweezers through an opening in the mesh container which can be manipulated by the user to target the jet of steam onto the jewelry being cleaned.

U.S. Pat. No. 7,257,319 discloses a portable jewelry cleaning device that emits steam through a tube over the jewelry being cleaned. A containment device is optionally provided which catches any jewelry which is dislodged during cleaning. Unlike the disclosure in U.S. Pat. No. 6,338,350, this device houses a steam generator and is self contained. A water reservoir is also housed within the device which is filled by the user.

U.S. Pat. No. 6,076,538 discloses a jewelry cleaning kit and method wherein the user secures the jewelry in holding basket and dunks the basket with the jewelry into a cleaning solution. The basket with the jewelry is then placed in an automatic dishwasher for a final cleaning with a water spray and steam.

It has also been proposed to heat cleaning fluids, including water and cleaning solutions, by heating the same in a microwave oven. In U.S. Pat. No. 9,365,809 to Maiuri Cleaning Solution for Smoking Paraphernalia and Method are disclosed in which identified cleaning solutions, alone or diluted with water, are heated prior to being applied to a soiled surface for cleaning. The patent teaches placing the cleaning fluids or solutions in a microwave oven for different time periods to clean different tarnished surfaces, suggesting that the most effective temperature is approximately 180° F. The solution is then sprayed onto a soiled surface to be cleaned. It is suggested that different heating times ranging from 10-120 seconds in the microwave set on "high" for different solutions may be required to clean different levels of grime or soil surfaces using temperatures ranging from 120°-182° F. U.S. Patent 2005/0159326 to Holyworth discloses a Method for Cleaning Carpets and Other Surfaces by using a vessel containing a cleaning composition placed into a microwave oven and heated to a temperature of approximately 90-220° F. after which the heated cleaning composition is applied onto the soiled surface by a means of a spray dispenser.

In U.S. Pat. No. 2,141,713 to Hensler et al a machine is disclosed for cleaning jewelry that uses a mounting panel for supporting the machine on a vertical surface, such as a wall, including a motor secured to the panel. A vertical shaft of which extends downwardly to supporting a basket into which items to be cleaned may be placed. A non-heated cleaning solution is placed in a liquid non-circular shaped container and the basket is submerged in the cleaning solution, after the container is secured to the panel, so that the basket is positioned "off center" to produce a rotation of the cleaning solution to physically impinge against the items to be cleaned. This machine is not portable and cannot be used to sanitize the items to be cleaned. Furthermore, using a motor to rotate the basket requires access to an electrical outlet or hardwired connection to a source of electricity.

In U.S. Pat. No. 5,876,513 to Frankson a holding basket receives items to be cleaned. The basket is placed into a cleaning solution to coat the jewelry with the solution after which the basket with the items are placed into a dishwasher and run through wash and dry cycles that removes the cleaning solution and grime from the items in the basket. This solution requires a dishwasher, is clearly not portable and the effectiveness of cleaning will be a function of the temperature of the hot water supply delivered to the dishwasher. The mentioned temperatures of tap water heated to "below 120° F." would not be adequate to sanitize the jewelry by the proposed method.

SUMMARY OF THE INVENTION

It is an object of the invention to provide a cleaning device for jewelry and small items or parts that is simple in construction and economical to manufacture.

It is another object of the invention to provide a cleaning device that is portable and can be used anywhere.

It is still another object of the invention to provide a portable cleaning device that is easy and convenient to use.

It is yet another object of the invention to provide a portable cleaning device as the previous objects that can clean and sanitize jewelry and other small parts.

It is further object of the invention to provide a portable cleaning device the effectiveness of which can be increased by heating a cleaning solution in a container that can be heated in a microwave oven to a temperature of at least 170° F.

It is still a further object of the invention to provide a portable device of the type under discussion that can optimize cleaning action by utilizing both mechanical and chemical means for removing surface contaminants and germs including, bacteria and potentially other pathogens.

It is yet a further object of the invention to provide a standalone portable cleaning device that is safe to use and handle notwithstanding the ability the use of relatively high temperatures of cleaning solutions within the device to sanitize items to be cleaned.

It is an additional object of the invention to provide portable cleaning device of the type aforementioned that provides a visible indication to a user when a cleaning fluid within the cleaning device has attained or reached a sanitizing temperature in excess of 170° F. without the need of thermometers or other temperature monitoring and indicating devices.

It is still an additional object of the invention to provide a portable cleaning device that is a standalone device that does not require a power source after the device has been heated in a microwave oven to a desired temperature and that can be manually operated both to sanitize and/or clean jewelry and the like.

It is yet an additional object of the invention to provide a portable cleaning kit including accessories that can be used to clean jewelry and other like small parts easily and conveniently on any surface, a countertop, a sink or the like.

To achieve the above and other objects that will become evident to those skilled in the art a portable cleaning device comprises: a generally cylindrical container for receiving a fluid to a predetermined level and defining a container axis and having a bottom wall and a top opening at opposing axial ends along said container axis. A basket is provided for supporting items to be cleaned and dimensioned to be removably receivable within the container, the basket defining a basket axis that is substantially coextensive with the container axis when the basket is received within the container and is configured to be rotatably supported for rotation on the bottom wall about said axes when received within the container. Spinning means is provided for spinning the basket on the bottom wall about the axes when the basket is received within the container. Spinning of the basket within the container on the bottom wall when immersed in fluid below the predetermined level creates turbulence and agitates the fluid in contact with the items to be cleaned to dislodge soil particles and contaminants from the items to be cleaned.

In one preferred embodiment of the invention the cleaning device comprises: a microwavable container for receiving a cleaning solution to a predetermined level and that defines a container axis and has a bottom wall and top opening at opposing axial ends along the container axis for heating the solution in a microwave oven to a temperature in excess of approximately 170° F. A basket is provided for supporting items of jewelry is dimensioned to be removably receivable within the container, the basket defining a basket axis that is substantially coextensive with the container axis when the basket is received within the container and is configured to be rotatably supported for rotation on the bottom wall about the axes when received within said container. A manual spinning mechanism is provided for spinning the basket on the bottom wall about the axes when the basket is received within the container. By manually spinning the basket within the container on the bottom wall when immersed in heated cleaning solution below the predetermined level creates turbulence and agitates the cleaning solution in contact with the items to be cleaned to dislodge soil particles and contaminants from and sanitize the surfaces of the items to be cleaned.

A cleaning kit for cleaning jewelry and small parts includes a container, preferably microwavable, a basket having a tray for supporting items of jewelry or small parts to be cleaned a manual spinning mechanism for spinning the basket; a metal disc on the tray on which the items to be cleaned are placed, and an optional small parts stabilizer, a cover or lid for the container; a sink safety strainer or caddy; a rinse bubble and a cleaning utensil that includes a brush and pick at opposing ends.

BRIEF DESCRIPTION OF THE DRAWINGS

Those skilled in the art will appreciate the improvements and advantages that derive from the present invention upon reading the following detailed description, claims, and drawings, in which:

DETAILED DESCRIPTION

Figure 1:
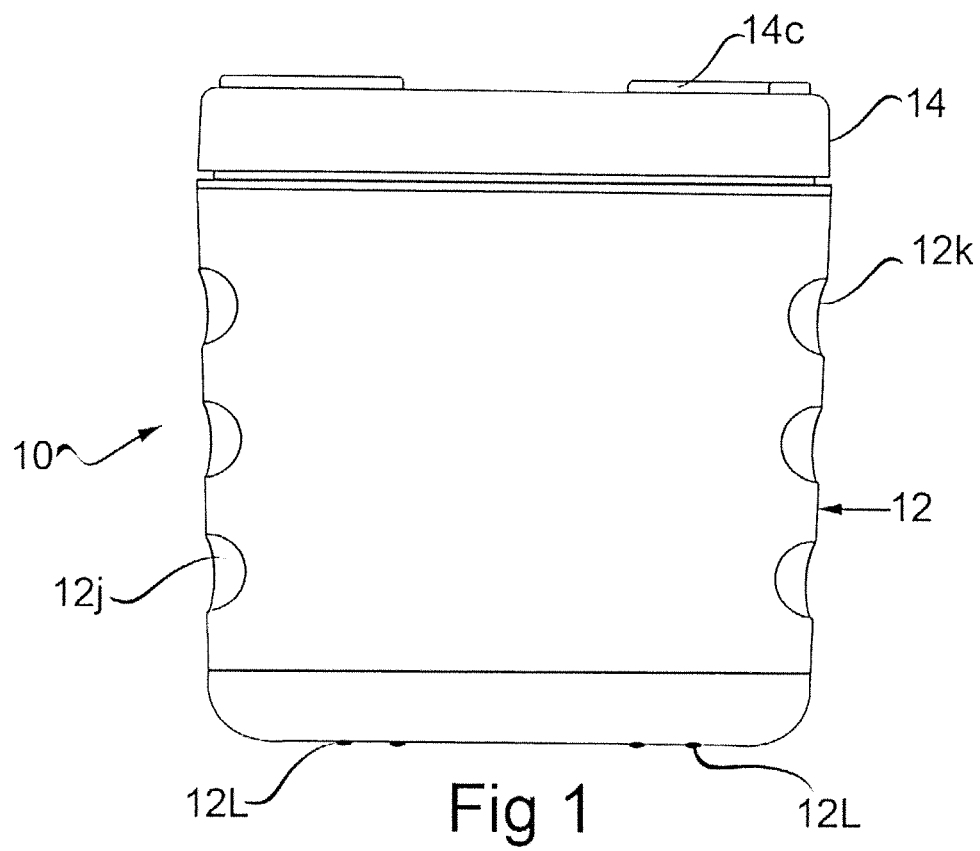
FIG. 1 is a front elevational view of a container forming part of the cleaning device in accordance with the invention.

Referring now specifically to the figures, in which identical or similar parts are designated by the same reference numerals throughout, and first referring to FIG. 1 a first major component of the cleaning device in accordance with the invention includes a generally cylindrical container 10 for receiving a fluid in a jar or tub 12. The container also includes a lid 14 that can be threadedly attached to the jar by means of conventional threads or other means. The details of the jar 12 and lid 14 will be described in more detail below. Besides the cylindrical container 10 another major component of the cleaning device is a spinning mechanism or carousel receivable within the jar 12, as to be described.

Figure 1A:
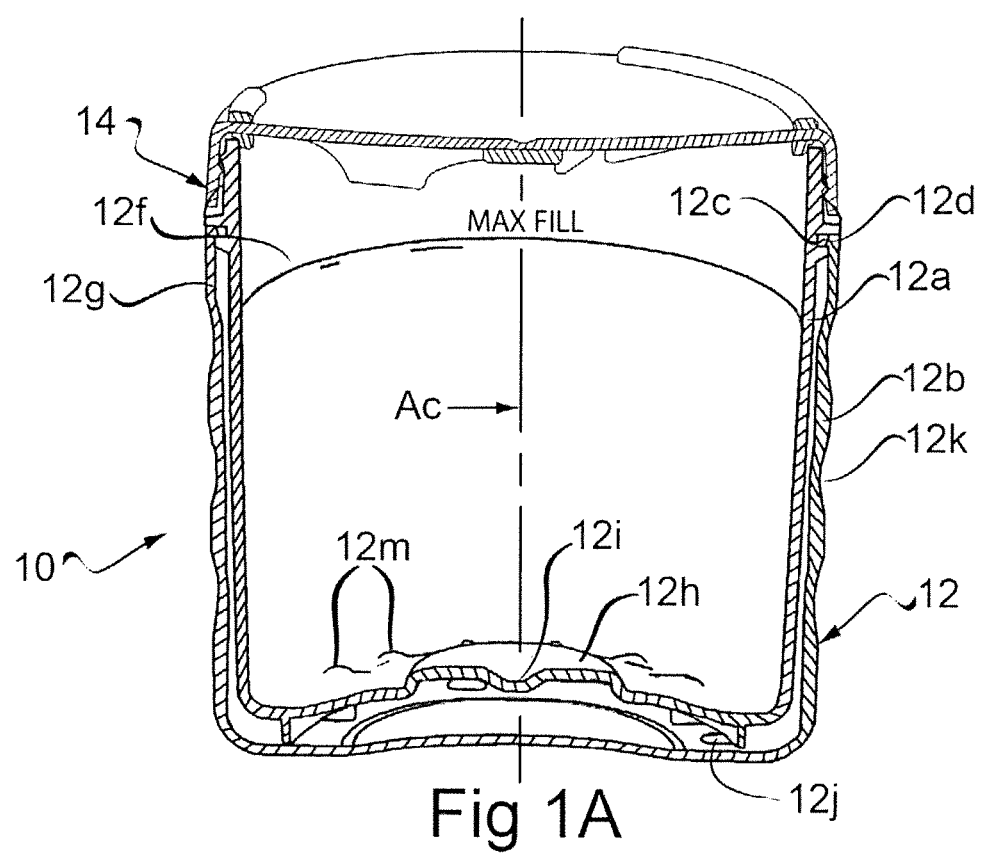
FIG. 1A is a perspective view of the container shown in FIG. 1, partially in section, to show the double wall construction and central elevation on the bottom wall of the container.
Figure 1B:
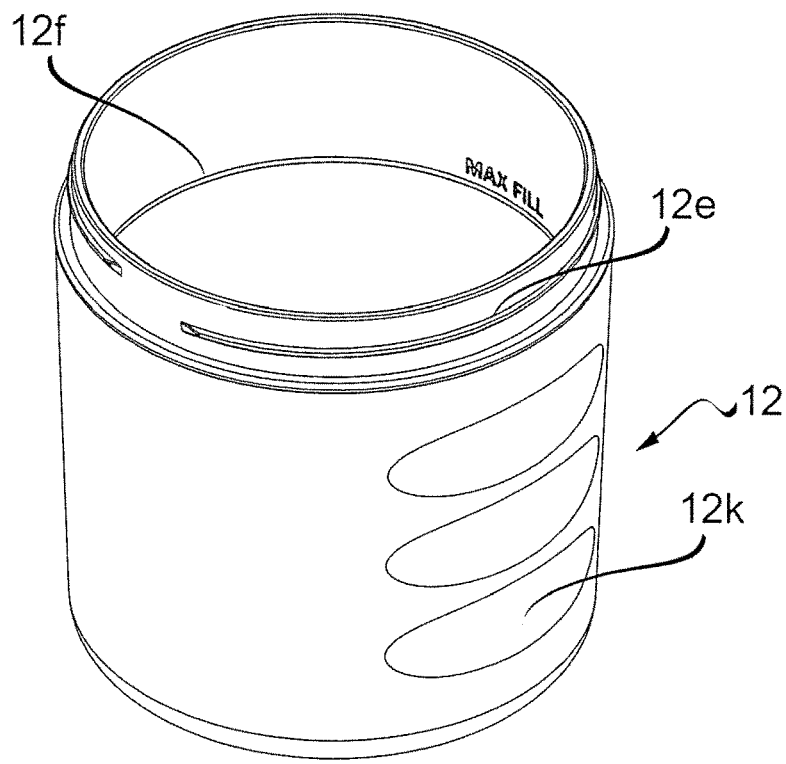
FIG. 1B is a perspective view of the lower part of the container—jar or tub—shown in FIG. 1.
Figure 1C:
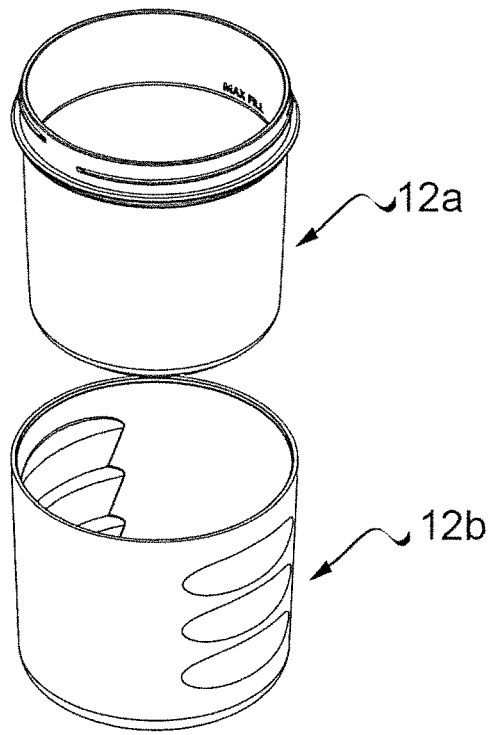
FIG. 1C is an exploded view of the lower part of the container shown in FIG. 1B with the inner shell of the container removed from the outer shell.
Figure 1D:
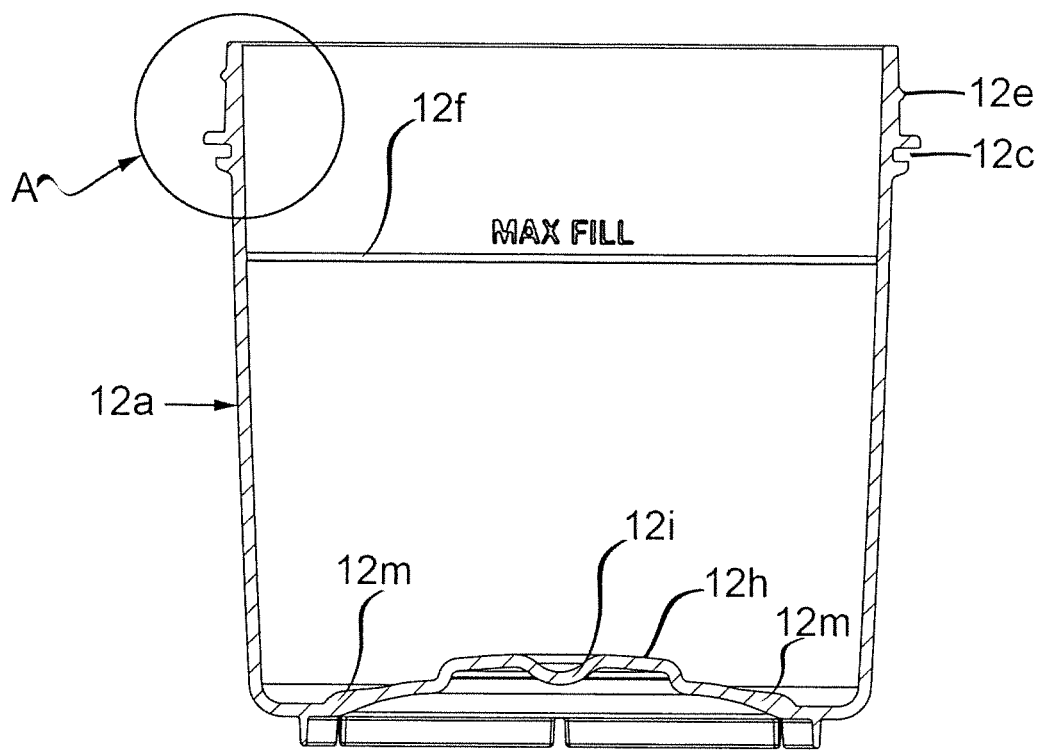
FIG. 1D is a cross sectional view of the container shown in FIGS. 1-1C, with the outer shell removed, shown in longitudinal or axial section.
Figure 1E:
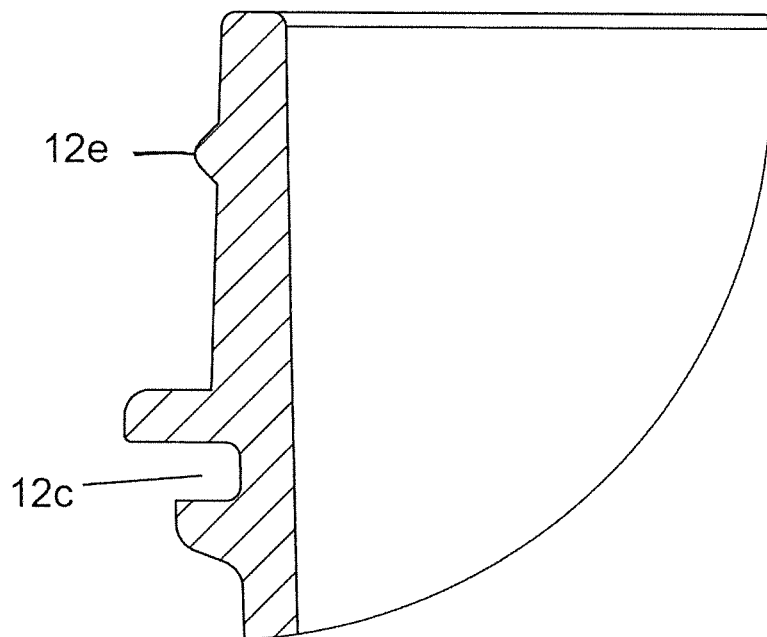
FIG. 1E is an enlarged detail of the region A shown in FIG. 1D.
Figure 1F:
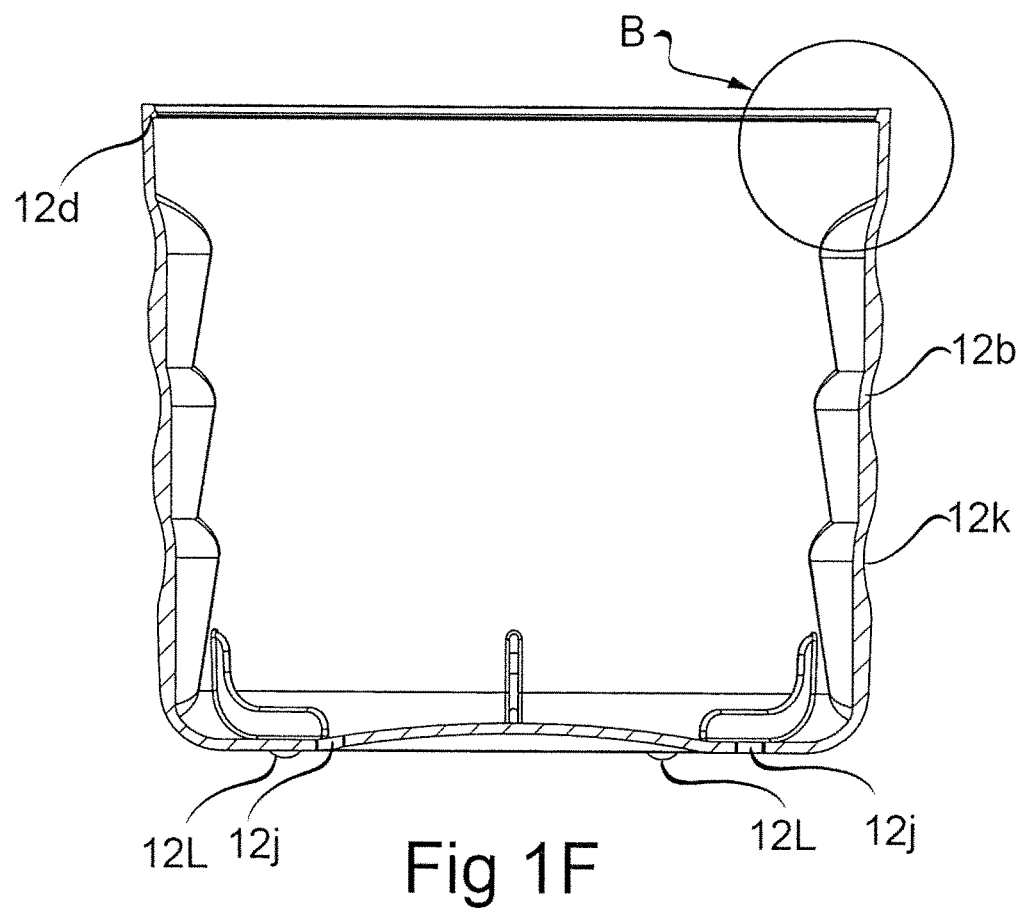
FIG. 1F is a longitudinal or axial section of the outer shell of the container shown in FIGS. 1 and 1A.
Figure 1G:
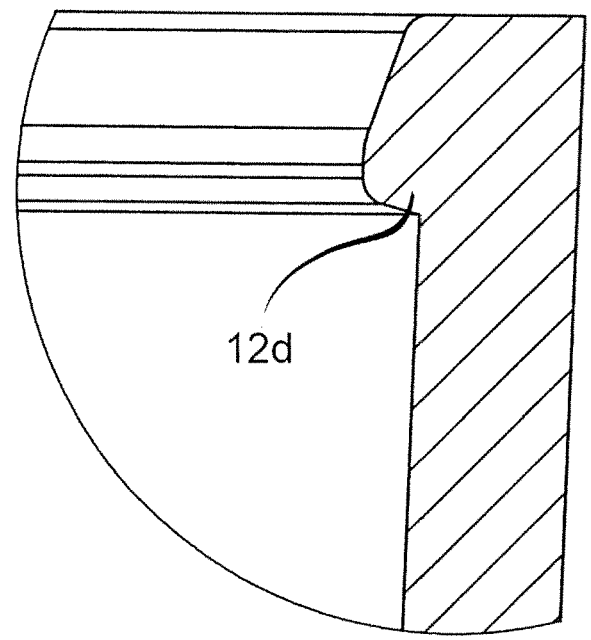
FIG. 1G is an enlarged detail of the region B shown in FIG. 1F.
Figure 9A:
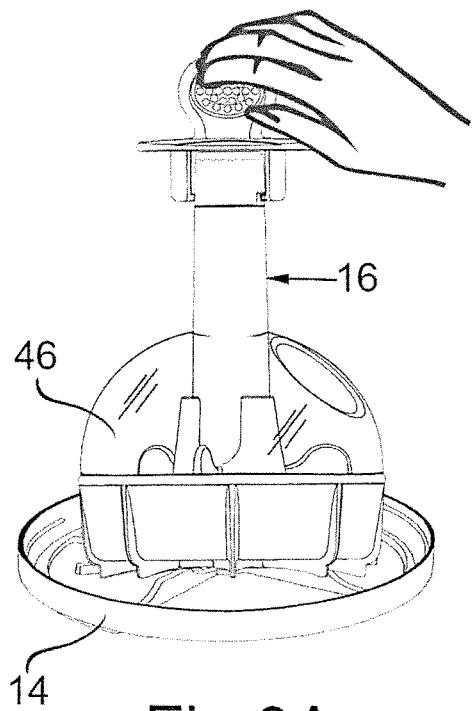
FIGS. 9A-9X are views illustrating steps in the use and operation of the portable cleaning device to clean jewelry and other small parts.

Referring to FIGS. 1-1C the jar or tub 12 includes a generally cylindrical inner shell 12a. An outer shell 12b encloses the inner shell 12a. The axial height of the inner shell corresponds to the height of the outer shell of the inner shell but includes an annular or cylindrical extension forming a threaded region. A circumferential grove 12c is provided on the exterior surface of the inner shell 12a. The upper edge of the outer shell 12b is provided with an inwardly directed annular rim or lip 12d preferably tapered to facilitate the rim to be snapped into the annular groove 12c to retain the two walled members in place once assembled. An outer thread 12e formed on the inner shell 12a extension is conventional and configured to mesh with an inner thread 14a (FIG. 1I) within the lid or cover 14. Preferably an inner marking 12f is provided as shown in FIG. 1A to designate a maximum fill line for filling of a fluid such as water, a cleaning solution or a mixture thereof. As shown in FIG. 1A, the inner and outer shells 12a, 12b are configured to provide an inner space 12g between the shells when assembled to provide thermal insulation to maintain the temperature of the outer shell 12b comfortable to the touch when gripping the container during use as to be described. As shown in FIGS. 1A and 1D the jar 12 has a bottom wall and a top opening at opposing axial ends along the container axis $A_c$. Provided on the bottom wall is a central raised portion 12h with a central depression 12i, that is shown in FIG. 1D. Provided around the central raised portion 12h are integrally molded spaced upwardly projecting tabs or protuberances (FIGS. 1A and 1D) that will be further described in connection with FIG. 9I. Holes 12j (FIGS. 1A and 1F) are formed in the bottom wall of the outer shell to allow any water as other fluid trapped between the inner and outer walls 12a, 12b to escape as well to prevent buildup of pressure between the walls when water or other fluid is heated in a microwave oven and turned into steam.

Figure 9B:
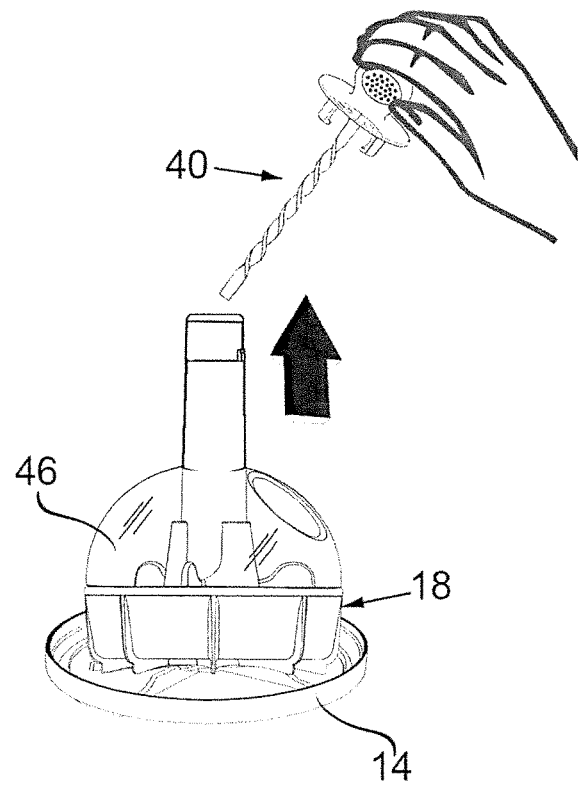
FIG. 9Y is a color change guide showing progression of color changes of the jar as the temperature is increased.
Figure 9C:
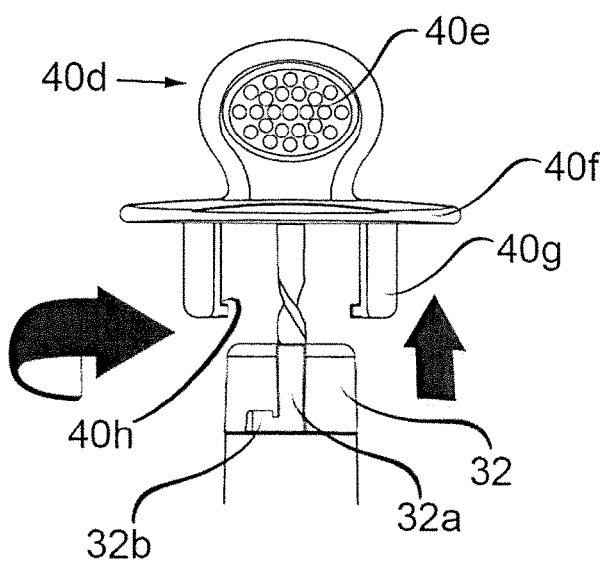
Figure 9D:
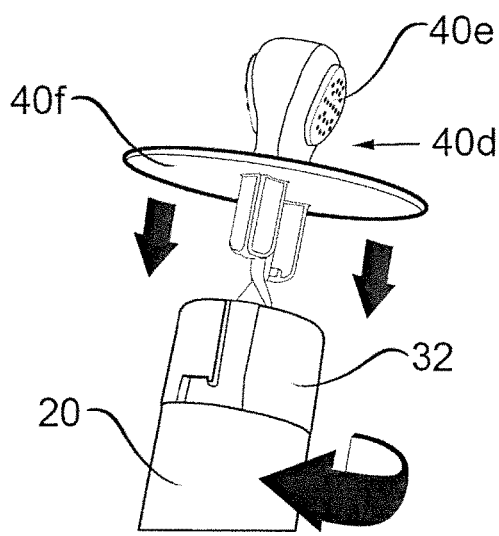

The cleaning device in accordance with the invention can be used with any fluids and cleaning solutions, with different degrees of advantage, at sanitizing and below sanitizing temperatures. However, best results and sanitation of the items to be cleaned are best obtained when the fluid or cleaning solution is heated to a temperature of at least 170° F. and preferably in excess of 170° F. Towards that end the inner and outer shells 12a, 12b may be formed of any suitable microwavable materials that can withstand these temperatures. Preferably, the inner and outer shells are formed of a plastic material, such as but not limited to a high temperature polypropylene. The inner and outer shells need to withstand the indicated temperatures without deformation or warping. Preferably, the thickness of the shells, the size of the insulating air gap or space 12g are selected to render the outer shell comfortable to the touch even when the temperature of the fluid within the inner shell is heated to sanitizing temperatures. Preferably, the outer shell is provided with a series of circumferential or elongated depressions 12k as shown in FIGS. 1A-1C to receive a user's fingers to provide reliable gripping of the container and prevent slipping thereof when removed from a microwave oven. Slip resistant feet 12L (FIGS. 1a and 1F) are provided at the bottom of the jar or tub 12 to prevent sliding movements when the cleaning is operated as described with reference to FIGS. 9A to 9X.

Figure 1H:
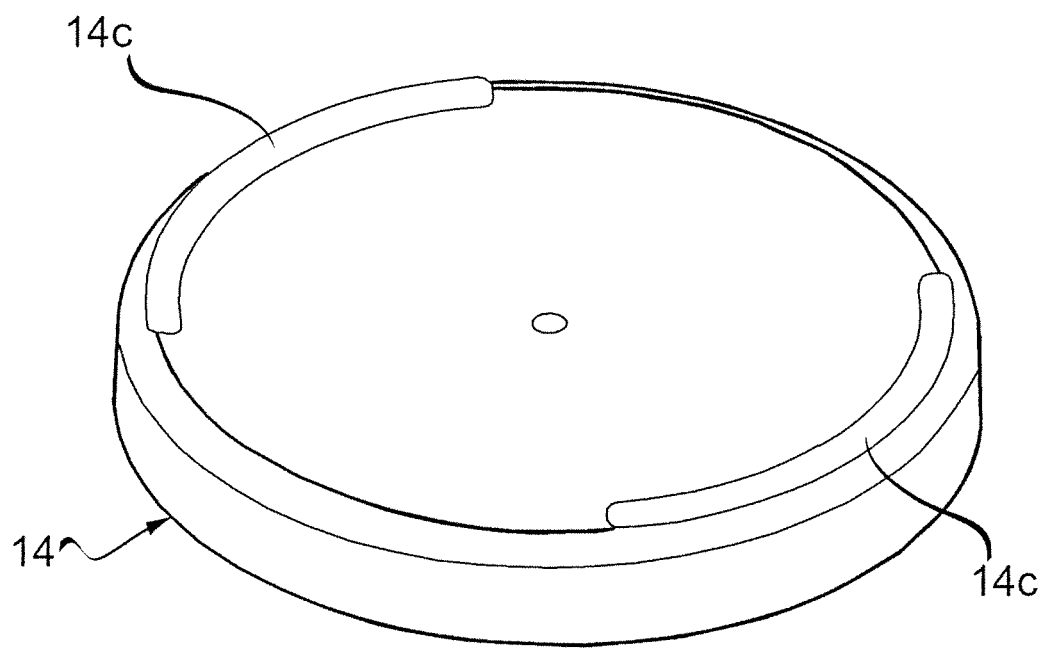
FIG. 1H is a perspective view of the upper or outer side of the lid or cover of the container shown in FIG. 1.
Figure 1I:
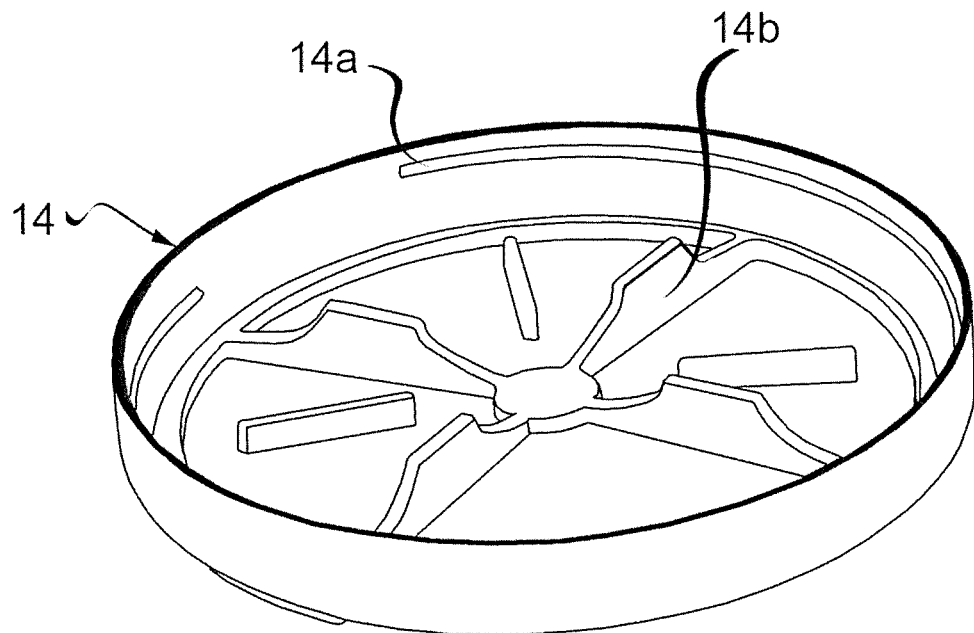
FIG. 1I is a perspective view of the underside or interior of the cover or lid shown in FIG. 1H.

Referring to FIGS. 1H and 1I, the lid 14 is provided with inwardly projecting santoprene tabs 14b that serve as rests for the carousel as to be described. Rubber slip-resistant lands 14c are provided on the other side of the lid when it serves as a base for the carousel on a countertop or other surface.

Figure 2:
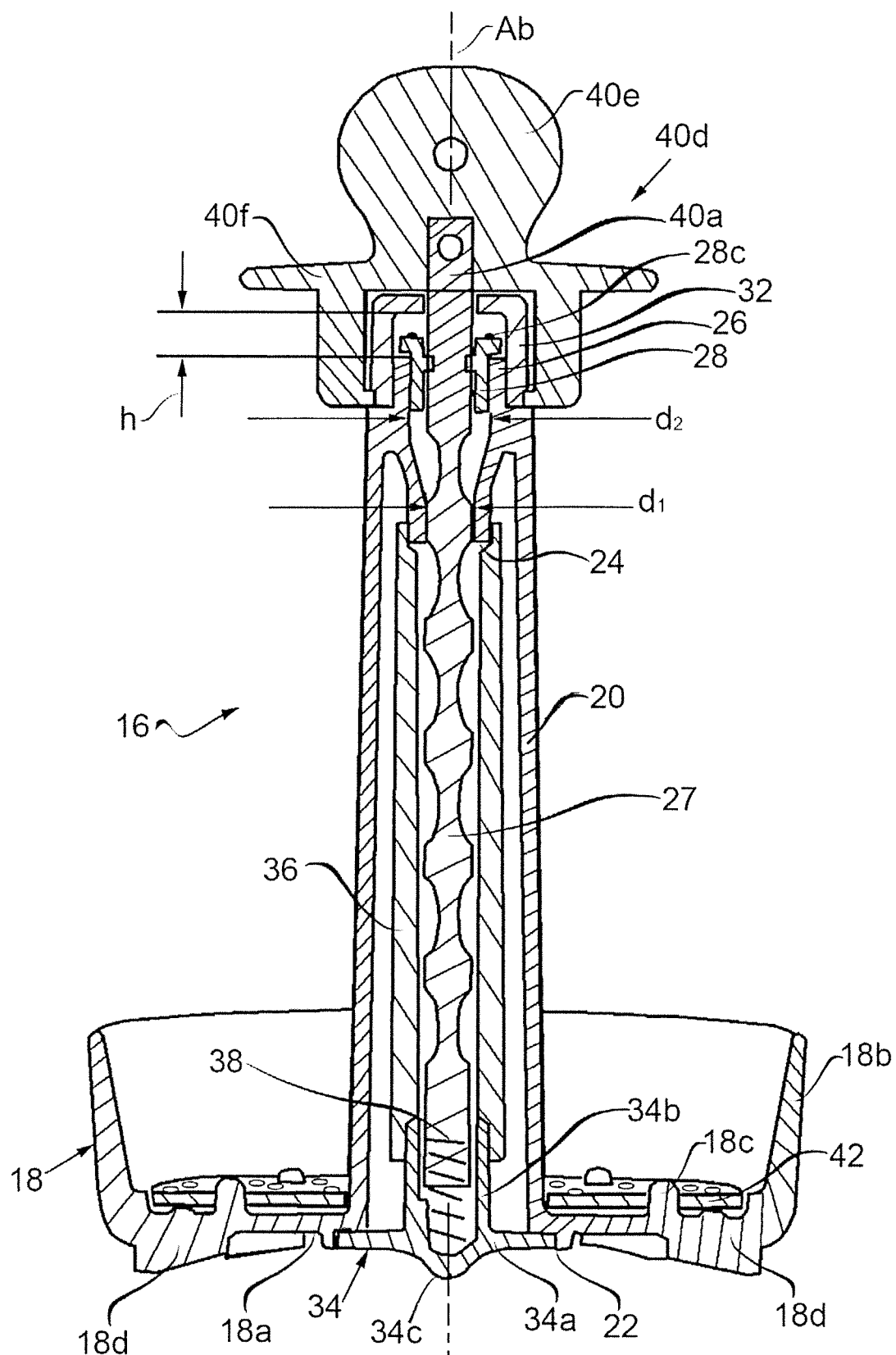
FIG. 2 is a longitudinal section of a jewelry supporting carousel assembly, including a basket with a support tray that includes a metal disc and a spinning mechanism, removably receivable within the container shown in FIG. 1, shown in the locked condition of the spinning mechanism.
Figure 2A:
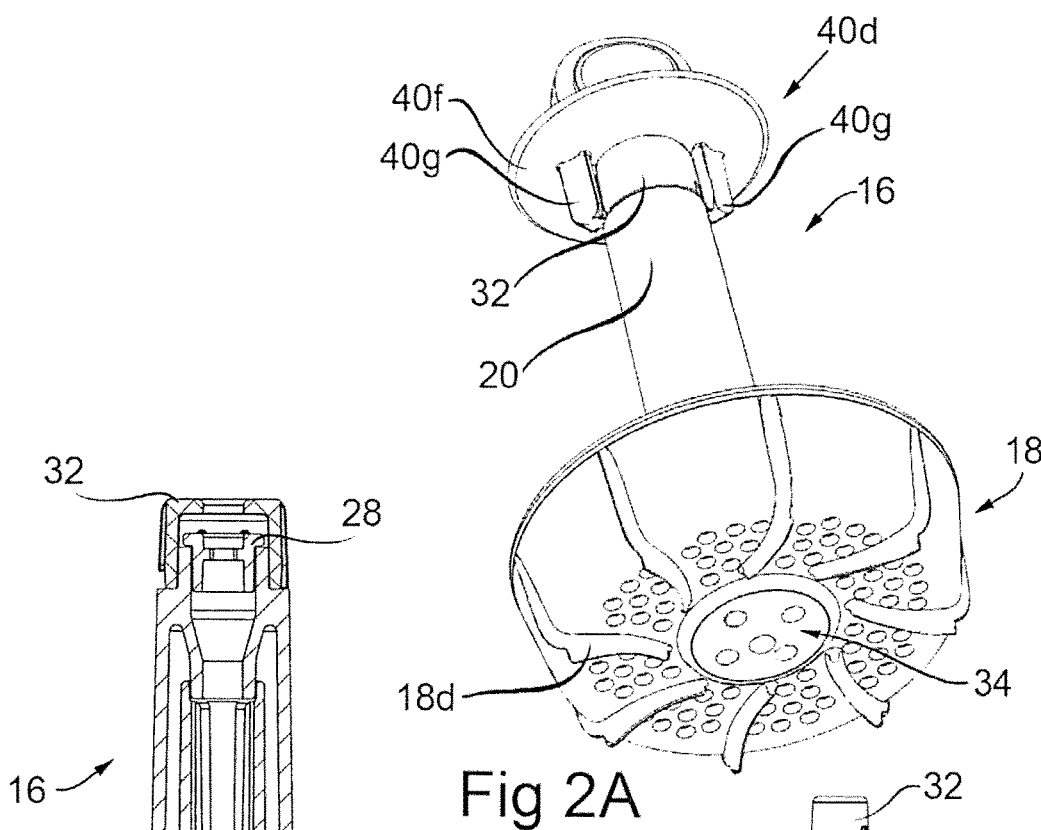
FIG. 2A is a perspective view of the spinning mechanism shown in FIG. 2 as viewed from the underside thereof.
Figure 2B:
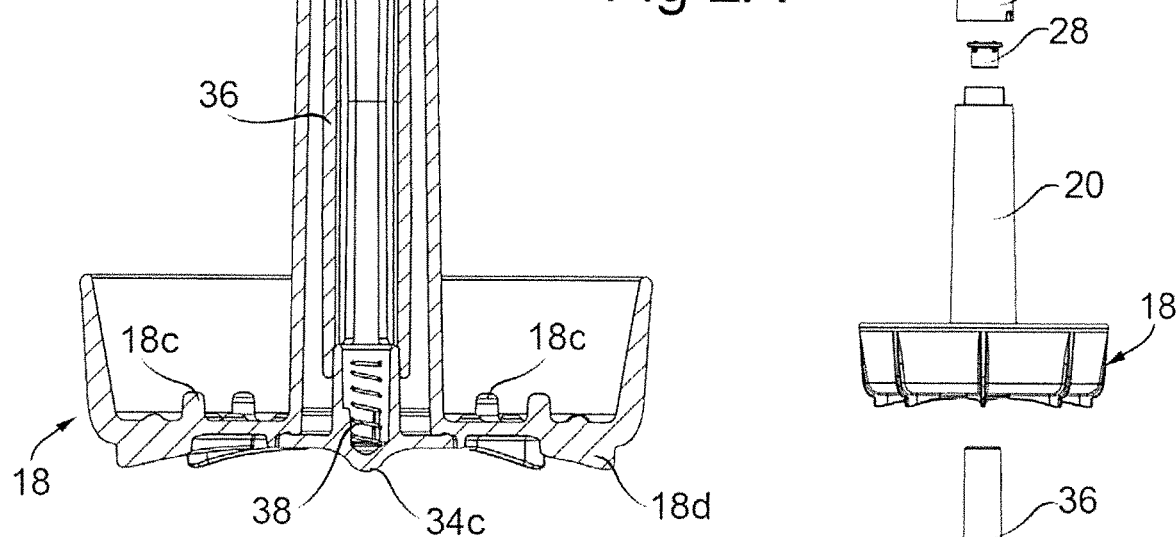
FIG. 2B is a longitudinal cross section of the spinning mechanism main body that includes a basket for supporting jewelry or other small parts to be cleaned and a central post for receiving a spiral plunger shaft shown in FIG. 2.

Referring to FIGS. 2-2B, a carousel or spinning mechanism 16 is a second major component of the cleaning device and includes a basket forming an annular tray 18 for supporting small items to be cleaned and dimensioned to be removably received within the jar 12, the basket defining a basket axis $A_b$ that is substantially coextensive with the container axis $A_c$ when the basket 18 is received within the jar 12. The basket 18 diameter is somewhat smaller than the inner diameter of the inner shell 12a to maximize the size of the basket while providing a clearance with the inner surface of the inner shell to allow the basket 18 to rotate freely about the axes $A_c, A_b$ without contacting the inner shell. The basket 18 includes a lower transverse base 18a and a generally cylindrical circumferential wall 18b. Projecting upwardly, as viewed in FIG. 2, from the base 18a are circumferentially spaced upwardly directed projections 18c and downwardly projecting generally radial circumferentially spaced fins 18d.

The base 18a is joined with an upwardly projecting central post or main body 20, preferably integrally formed with the base 18a at the lower end thereof as shown. An annular recess 22 is provided in the region where the central post 20 meets the base 18a. At the upper end of the central post or body 20, as viewed in FIG. 2, the upper free end is formed with a downwardly projecting tubular or annular extension 24 and an upwardly extending tubular or annular portion 26. The tubular extension 24 has an internal diameter $d_1$ and the tubular extension 26 has an inner diameter $d_2$ where $d_2$ is shown to be greater than $d_1$. The tubular extension 24 is dimensioned to receive a spiral plunger 27 with clearance to allow the plunger to move axially up and down through the tubular extension while maintaining its central position along the axis $A_b$. Provided along an upper edge of the annular or tubular extension 26 there are provided at least two sloping or inclined cam surfaces 20a (FIG. 2G) symmetrically arranged in relation to the axis $A_b$ to cooperate with a spin clutch 28 and having stop surfaces 20b so that the clutch can slide along the inclined surfaces 20a and be stopped by the stop surfaces 20b. The spin clutch 28 is provided with an annular rim 28a that has a diameter greater than $d_2$ and a number of outwardly projecting radial tabs 28b, equal to the number of cam surfaces 20a and stop surfaces 20b. The clutch 28 is provided with a central rectangular slot 30 (FIG. 2F) having a length and width dimensioned to receive the rectangular cross-section of the spiral plunger 27 with small clearance to allow the plunger to freely move upwardly and downwardly through the rectangular slot 30 with minimal friction. A cup-shaped clutch cap 32 is fixed to the outer surface of the tubular extension 26 as shown to provide sufficient axial clearance "h" (FIG. 2) to allow the spin clutch 28 to move up and down in response to vertical movements of the plunger 27 to disengage the tabs 28b from the cam surfaces 20a (FIG. 3B) when the clutch is raised to bring the rim 28a into contact with the cap 32 and engage the tabs with the cam surfaces when the clutch is lowered to bring the rim 28a into contact with the portion 26 of the post 20. When the spiral plunger is pushed downwardly to urge the radial or lateral projections or tabs 28*b* to slide on the cam surfaces 20*a* into engagement with the stop surfaces 20*b* to thereby engage and rotate the clutch and, therefore, likewise cause the central post or main body 20 to rotate when the spiral plunger is forced downwardly. When the spiral plunger 27 has reached its lower most position, as shown in FIG. 2, it can be manually raised, causing the spin clutch 28 to be raised above the inclined cam surfaces 20*a* formed within the upwardly extending tubular extension 26. Such engagement of the clutch allows the spiral plunger to be raised to an upper most position to again repeat the cycle by again pressing the plunger downwardly for continued rotation of the basket 18 by repeated engagement and disengagement of the clutch from the central post 20. Dots or small protuberances 28*c* (FIG. 2E) are spaced along the rim 28*a* that minimize small points of contact with the under facing surface of the cap 32 when the clutch 28 is in a raised position to ensure that the clutch does not stick to the cap when the plunger is in an extended position but drops when the plunger moves vertically downwardly.

Figure 2C:
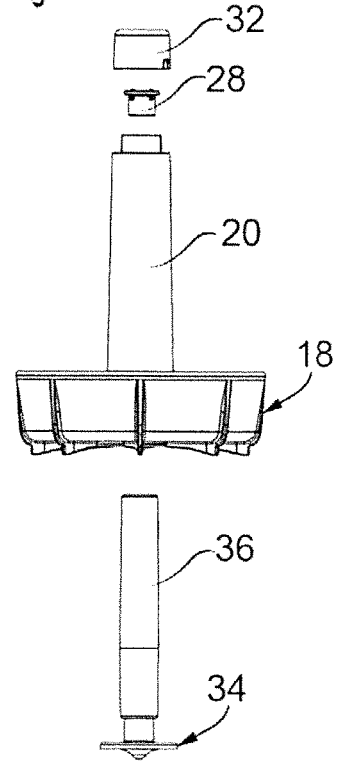
FIG. 2C is an exploded view of the component parts of the main body shown in FIG. 2B.
Figure 2D:
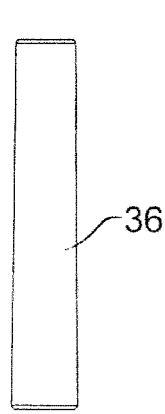
FIG. 2D is an exploded view of the inner tube forming part of the main body of the carousel shown in FIG. 2B and the component parts of the assembly.
Figure 2D:
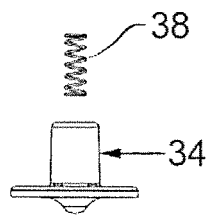
Figure 2E:
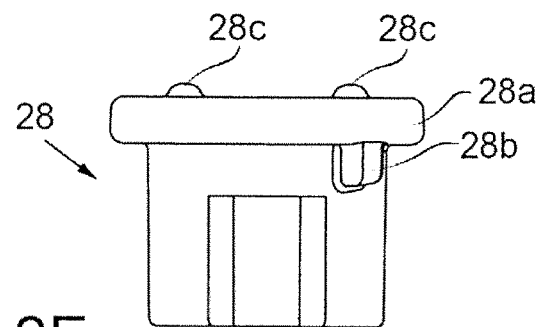
FIG. 2E is a side elevational view of a clutch for interacting with the central post of the carousel and a spiral plunger shaft for selectively rotating the carousel about the axis of the spinning mechanism.
Figure 2F:
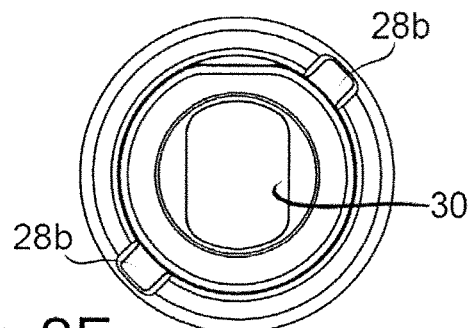
FIG. 2F is a bottom plan view of the clutch shown in FIG. 2E.
Figure 2G:
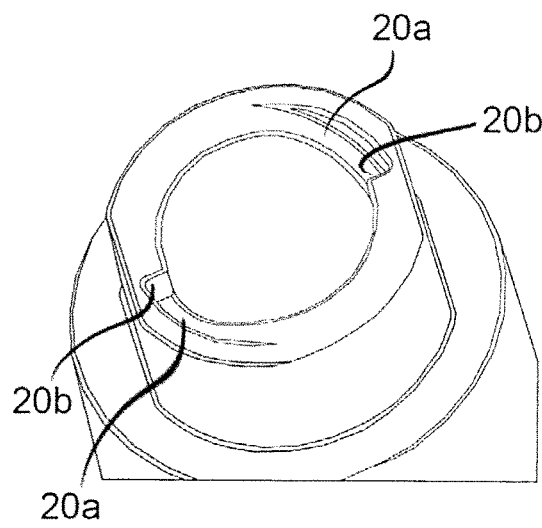
FIG. 2G is perspective view showing details of the inclined or sloping cam surfaces at the upper end of the central post of the main body of the carousel shown in FIGS. 2B and 2C.
Figure 2H:
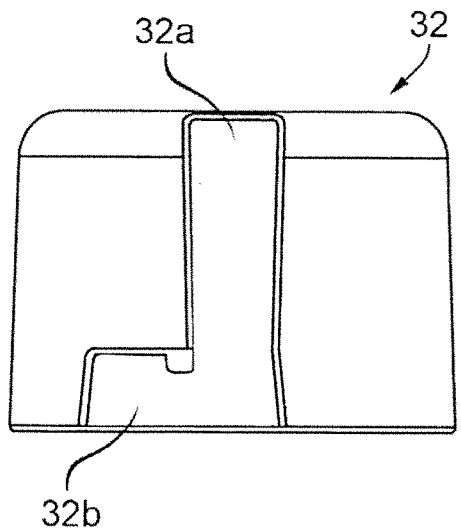
FIG. 2H is a side elevational view of the spin clutch cap mounted at the upper end of the central post, as viewed in FIG. 2, showing the recessed features or grooves for locking the spiral plunger shaft to the carousel central post to enable a user to lift the carousel by the finger grip at the exposed free end of the spiral shaft or plunger assembly and removing the carousel from the container.
Figure 2I:
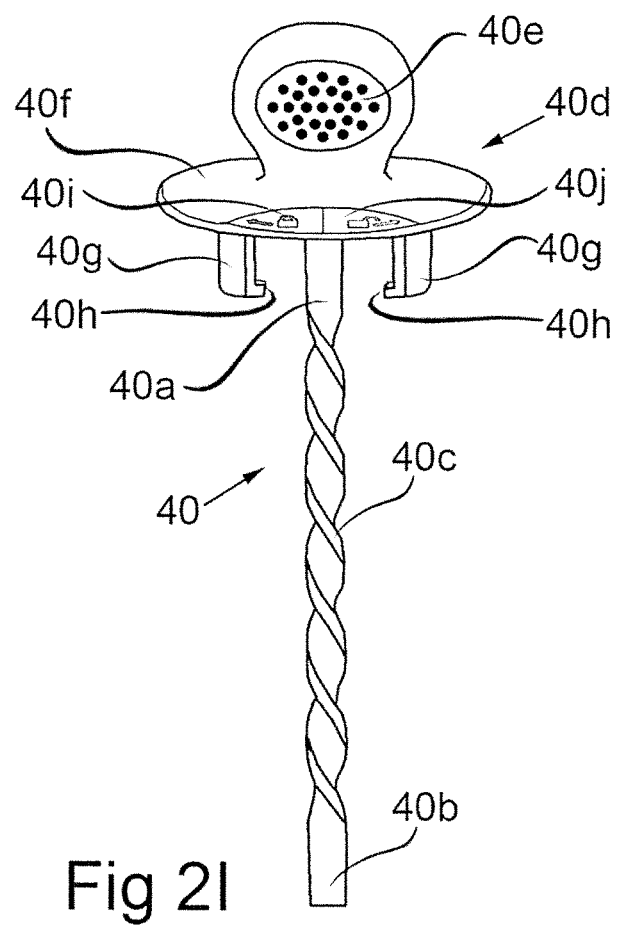
FIG. 2I is a perspective view of the spin plunger assembly including handle with finger grip and spiral plunger shaft, illustrating the diametrically opposing depending locking members that interact with the grooves or surface features shown in FIG. 2H.

Preferably, an inner tube 36 is provided, as shown in FIGS. 2, 2B and 2C that extends from the inwardly extending tubular extension 24 to a pivot plug 34 that includes a disc portion 34*a*, an inwardly-directed central tubular extension 34*b*, and central or axial downwardly-directed boss 34*c*. The boss 34*c* is a downwardly projecting protuberance preferably provided with a generally rounded or pointed end as shown. The disc portion 34*a* is preferably adhered or otherwise affixed to the basket 18 at the annular recess 22. A compression spring 38 is positioned axially within the pivot plug central tubular extension 34*b* and maintained centered by means of circumferentially spaced axial fins 34*d* (FIG. 2K). The spring 38 engages the lower most end of the spiral plunger 27 when it reaches its lowermost position to initiate an upward movement of the plunger. The elements or the components described in conjunction with FIG. 2 will be defined or denominated as a spin mechanism. The spin mechanism is generally similar to the spin mechanisms used in toy spinning tops and operates substantially in the same way.

Spinning the basket 18 on the boss 34*c* within the jar 12 filled with a fluid, aided by the radial fins 18*d*, will create a degree of turbulence within the fluid especially if the basket is caused to rapidly rotate relative to the fixed container jar 12, resulting in mechanical removal of debris and contaminants from items placed on the tray of the basket 18.

Depending on the nature and properties of the fluids or cleaning solutions used spinning of the carousel can also help to neutralize some or most contaminants. In a presently preferred embodiment of the invention there is also provided a metal disc 42 with circular holes 42*a* (FIG. 2N) dimensioned and arranged to receive the circumferentially spaced projections 18*c* on the basket 18 to rotate therewith. Preferably, the metal disc 42 is also provided with an array of additional distributed holes 42*b* to increase its surface area. Selection of an appropriate cleaning fluid in conjunction with an appropriate metal disc 42 can be effective both at ambient temperature or at an elevated temperature, with different degrees of advantage. Preferably, the container with the fluid is heated in a microwave oven to a temperature of at least 170° F. and preferably above 170° F. The cleaning solution advantageously includes a relatively strong base, such as sodium carbonate that dissolves and ionizes in water, acts as an alkaline that disassociates into the weak carbonic acid and a stronger alkaline sodium hydroxide. The sodium carbonate solution provides the ability to attack metals such as aluminum with the release of hydrogen gas. The release of hydrogen gas provides a second or additional mechanical mechanism for dislodging dirt and surface contaminants from metal parts placed within the tray or basket 18. The sodium carbonate is also useful as an electrolyte that acts as a good conductor in the process of electrolysis, creating carbonate ions that allows a small electrolytic current to flow. Hydrogen ions produced by this reaction reduce sulfide ions, for example, restoring silver metal. Disc 42, therefore, should be formed of a relatively active metal with increased ability to oxidize, such as aluminum, zinc, and nickel that can clean reducing metals that have the ability of being reduced, such as silver, platinum and gold. The oxidation reaction, for example, drives the reduction of silver. In this case, aluminum is an oxidizing agent reducing silver sulfide to elemental silver while forming aluminum sulfide. A heated fluid or liquid, such as boiling water, with or without an ionizable salt, increases the reaction when the solution temperature is higher. Aluminum in pure water would not remove silver tarnish because there is a film of aluminum hydroxide that stops the oxidation reaction. Sodium bicarbonate removes the surface film of aluminum hydroxide by dissolving it to expose fresh metallic aluminum ready for oxidation. Dissolving the sodium bicarbonate also increases the ionic strength of the solution, which increases the rate of the reaction.

Figure 2J:
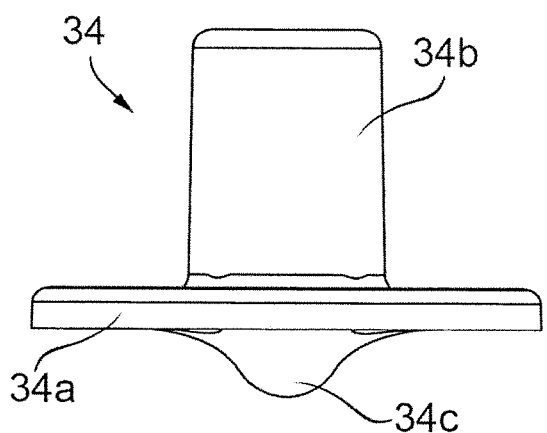
FIG. 2J is a side elevational view of the pivot plug forming a pivot for spinning the carousel on the bottom wall of the container.
Figure 2K:
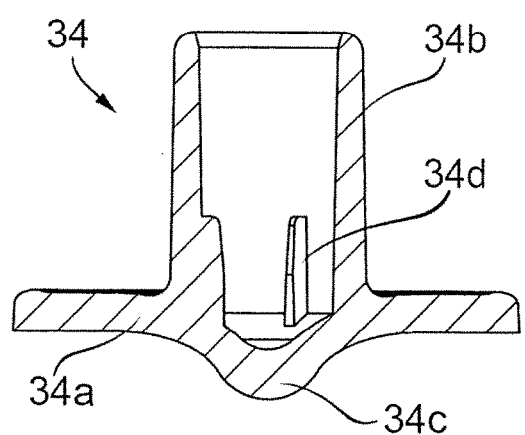
FIG. 2K is a longitudinal section of the pivot plug shown in FIG. 2J, illustrating the positioning or guide members for centering a compression spring that forms a part of the spinning mechanism.

Referring to FIGS. 2J and 2K, details of the pivot plug 34 are shown including the disc portion 34*a* and the tubular extension 34*b*. The central boss or protuberance 34*c* extends in a direction opposite to the direction of the tubular extension 34*b* and is provided with a pointed or rounded end 34*c* suitable for point contact to minimize friction when spun or rotated on the bottom wall or central raised portion 12*h* of the jar 12, when received and supported within the central depression 12*i*. At least three spring centering fins or tabs 34*d* are provided at the inner end of the tubular extension 34*b* as shown.

Figure 3A:
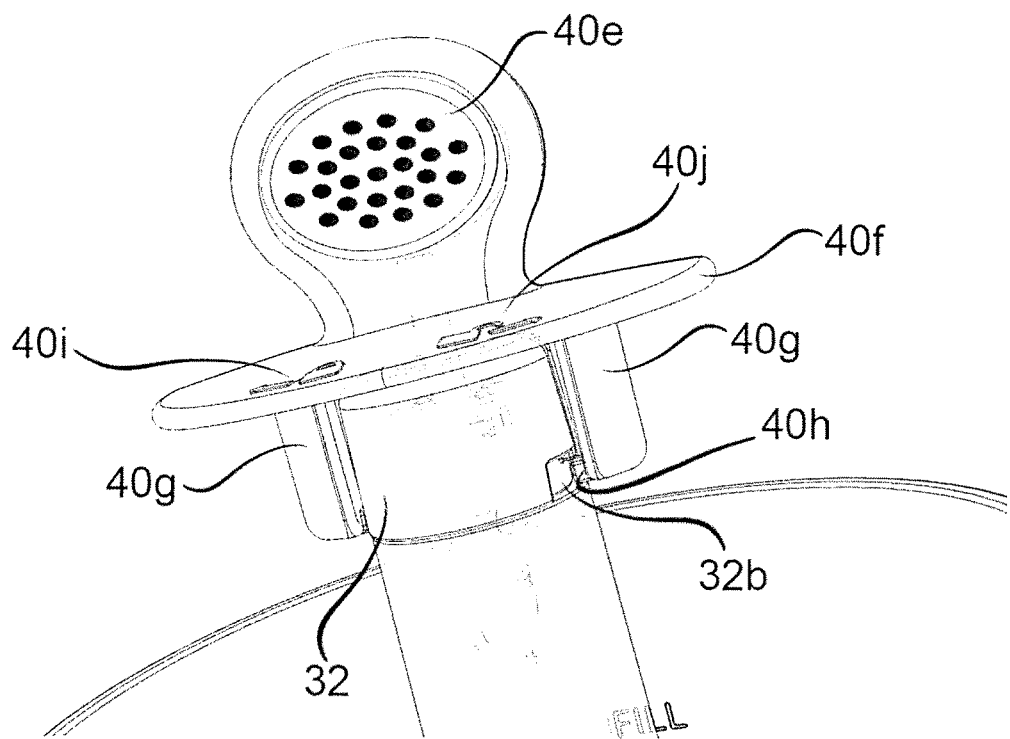
FIG. 3A is an enlarged perspective view of the upper portion of the spinning mechanism showing the plunger assembly in a locked condition to secure or fix it to the clutch cap to allow the spinning mechanism to be lifted from or introduced into the container shown in FIG. 1.
Figure 3B:
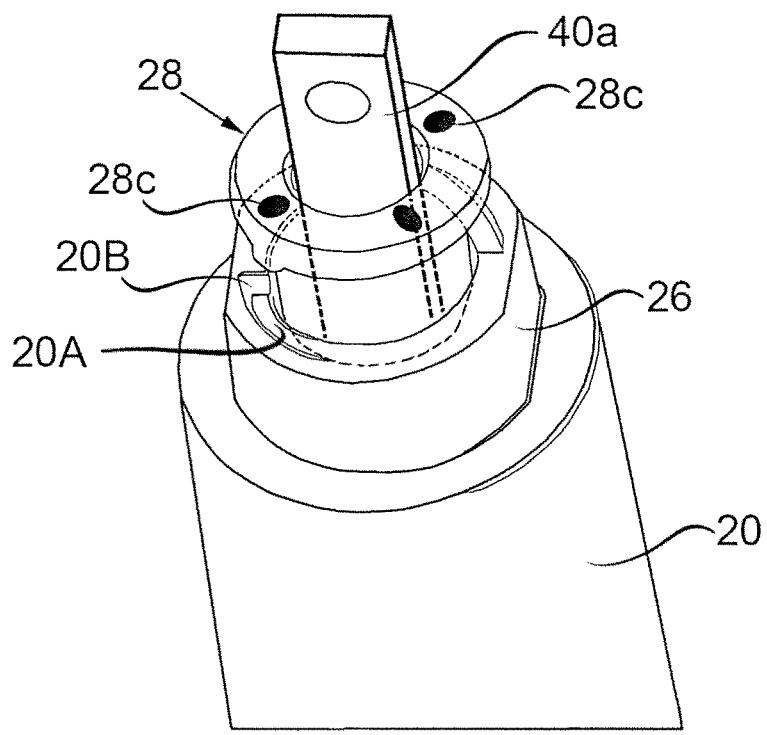
FIG. 3B is an enlarged perspective view illustrating the position of the clutch when the spiral plunger is lifted to disengage the clutch from the inclined or cam surfaces on the central post.

Referring to FIG. 2I the spiral plunger 40 includes a flat upper end 40*a* and a flat bottom end 40*b*, and an operative spiral portion 40*c* therebetween. A handle 40*d* is fixed to the upper end 40*a* and preferably provided with a finger grip with insulating pads 40*e*. A transverse radial disc portion 40*f* serves both to protect the user's hand from potentially hot cleaning fluids as well as for supporting opposed downwardly extending axial arms 40*g* each of which includes an inwardly directed radial locking tab or finger 40*h*. The arms 40*g* and fingers 40*h* are configured and dimensioned to be selectively receivable within diametrically opposite surface or exterior axial grooves 32*a* in the cap 32, when moved downwardly, and circumferential grooves 32*b*, when rotated relative to the spin clutch cap 32 to provide a bayonette-type connection to quickly and easily selectively lock the spiral plunger 27 to the central post or main body 20 or disengage it therefrom (FIG. 3A). The disc portion 40*f* is advantageously provided with markings 40*i* and 40*j* (FIGS. 2I and 3A) that respectively indicate to a user the clockwise and counter-clockwise rotations of the finger-grip 40*e* to lock and unlock the plunger assembly 40 to or from the spinning mechanism or carousel 16.

Figure 2L:
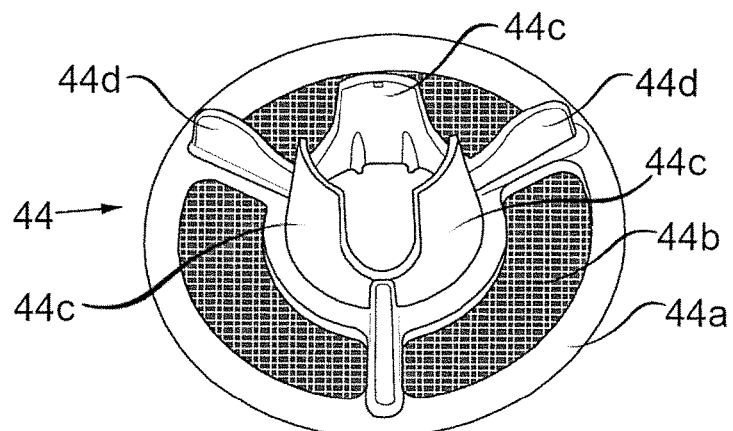
FIG. 2L is a perspective view of a small part stabilizer of the spinning mechanism to overlay and contact items of jewelry or small parts to prevent them from moving or shifting during spinning of the carousel.
Figure 2M:
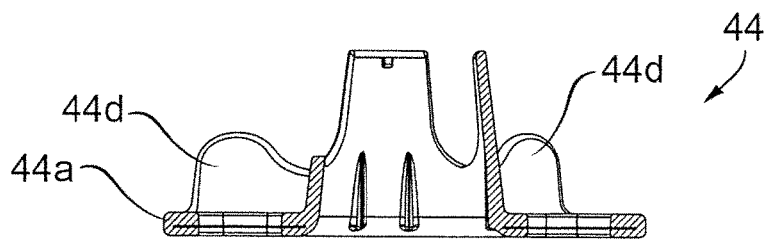
FIG. 2M is a side elevational view, in section, of the stabilizer shown in FIG. 2L.
Figure 2N:
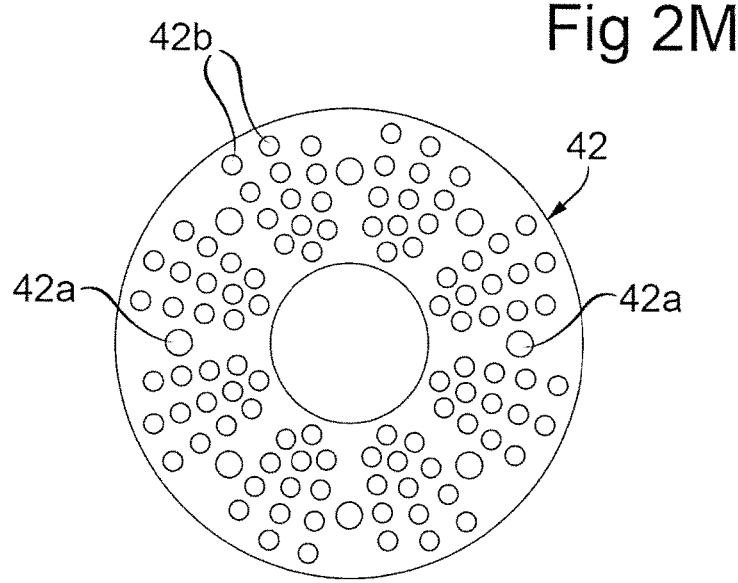
FIG. 2N is a top plan view of a metallic disc positionable on or within the tray of the basket or tray for supporting jewelry or other small parts.

Referring to FIGS. 2L and 2M a small part stabilizer 44 is shown that is generally disc shaped and dimensioned to be received within the tray of the basket 18. The stabilizer 44 includes a generally circular disc or platform 44*a* most of which is porous (e.g. mesh 44*b*) and includes somewhat tapered axial projections 44*c* dimensioned to frictionally engage the central post 20 along different axial positions along the post to accommodate jewelry or other small parts of different sizes by wedging the items to be cleaned between the disc or platform 44a and the tray of the basket 18. The axial projections 44c may be somewhat flexible and inwardly inclined to expand when placed over the post in frictional engagement. Jewelry or small parts are placed on the tray of the basket 18 directly or on the metal 42 disc. The stabilizer 44 is moved downwardly until there is contact between the stabilizer 44a and the items to be cleaned to prevent movements of the items to be cleaned when the basket 18 is rotated. The parts to be cleaned are maintained fixed on the tray as it rotates and the fluids impinge against the items to be cleaned. This is enhanced by providing radial fins 44d that promote agitation of the fluid.

Figure 2O:
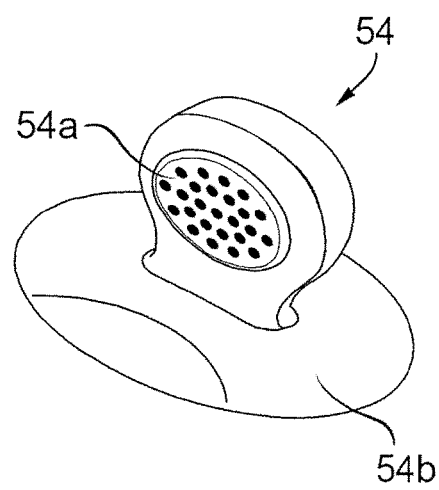
FIG. 2O is a perspective view of a resurfacing disc for resurfacing the metal disc shown in FIG. 2N.

Referring to FIG. 2O, a cleaning and resurfacing disc 54 may be used to resurface the disc 42, being provided with a finger grip 54a and a disc 54b provided with an abrasive surface (not shown) on the disc 54b.

The rinse bubble 46 and small parts stabilizer 44 are accessories that will be used as may be needed at user's discretion. This will depend on the size and type of the jewelry being sanitized and rinsed.

Figure 4A:
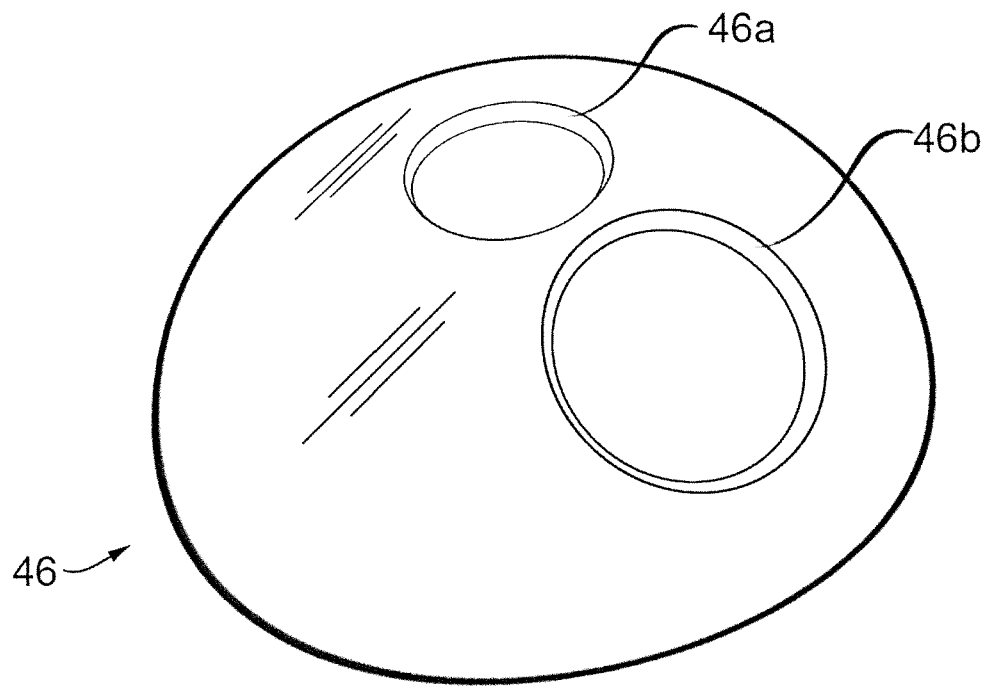
FIG. 4A is a perspective view of a rinse bubble that can be placed over the basket tray after items of jewelry or other small parts have been cleaned to rinse them by injecting a stream of water from a sink spray nozzle through a lateral opening.
Figure 4B:
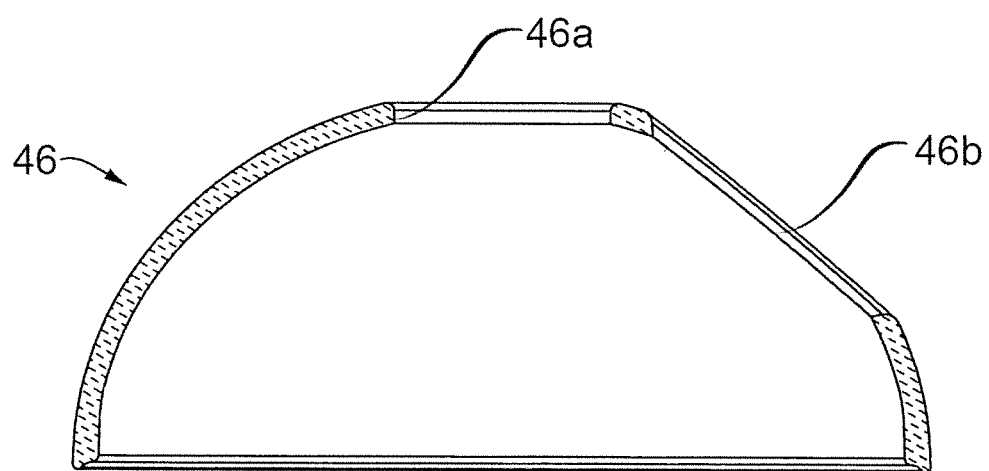
FIG. 4B is a side elevational view, in cross-section, of the rinse bubble shown in FIG. 4A.

Referring to FIGS. 4A and 4B, a rinse bubble 46 is shown, preferably made of transparent plastic. This is generally dome-shaped with a central opening 46a, dimensioned to receive central post or body 20, to cover the tray or base 18a and any objects thereon to be cleaned. A lateral opening 46b is provided dimensioned to receive a sink sprayer attachment to rinse off any chemical or cleaning solution residues on the jewelry to be cleaned without splashing water beyond the rinse bubble.

Figure 5A:
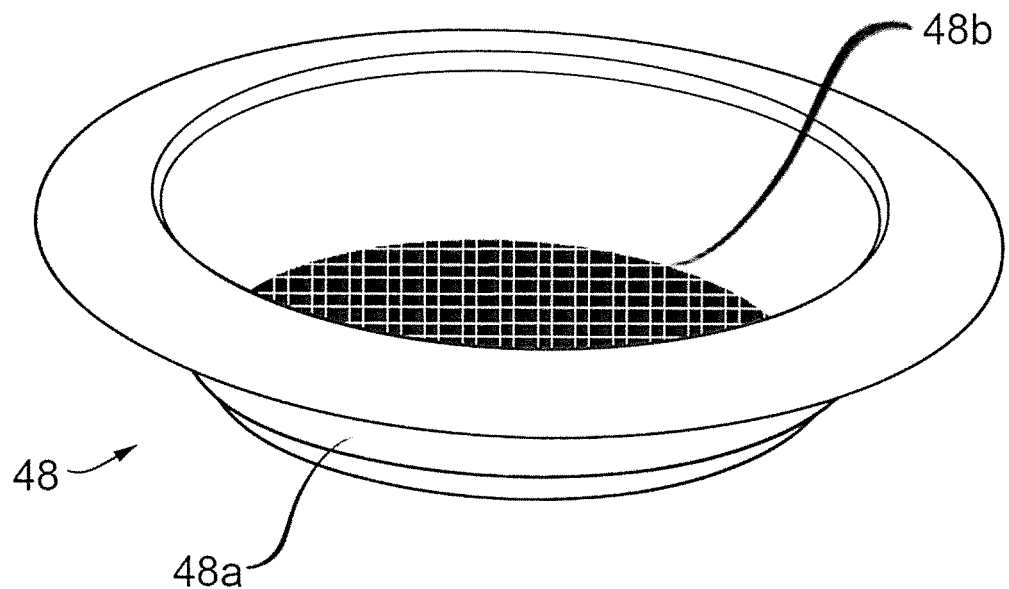
FIG. 5A is a perspective view of a safety strainer configured to receive the carousel over a water outlet or drain of a sink to prevent items that have been cleaned from inadvertently falling into the drain.
Figure 5B:
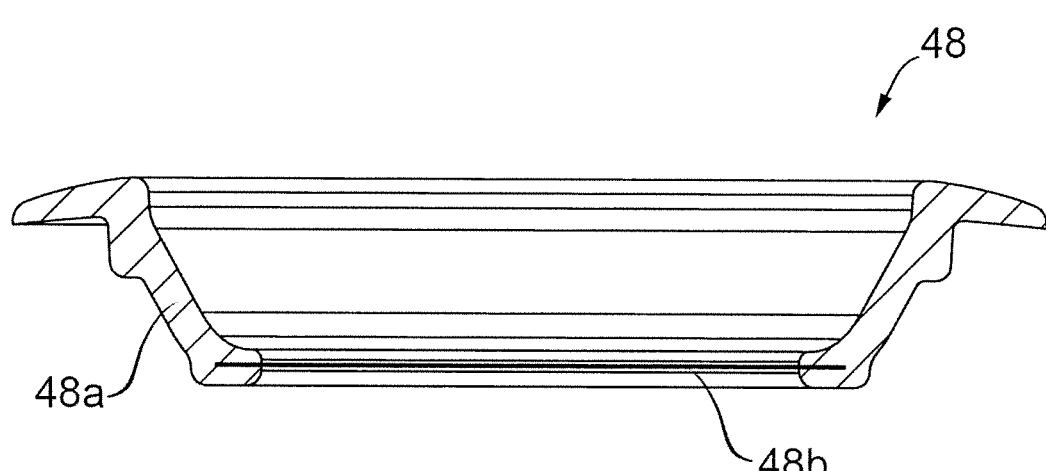
FIG. 5B is a transverse section of the safety strainer shown in FIG. 5A.

Referring to FIGS. 5A and 5B a safety strainer 48 is shown dimensioned to be placed over and having a portion thereof 48a fit within a drain of a sink. The circular strainer has a base formed of a meshed material 48b that allows the plunger mechanism to be removed from the jar 12 and securely positioned over the safety strainer with the rinse bubble in place. This allows a jet of water to be sprayed through the lateral opening 46b onto the parts to be cleaned and the water drained directly through the mesh 48b at the bottom of the basket and through the safety strainer without the danger of any jewelry or any small parts to be dislodged from the basket 18 and dropped and lost in the drain.

Figure 6A:
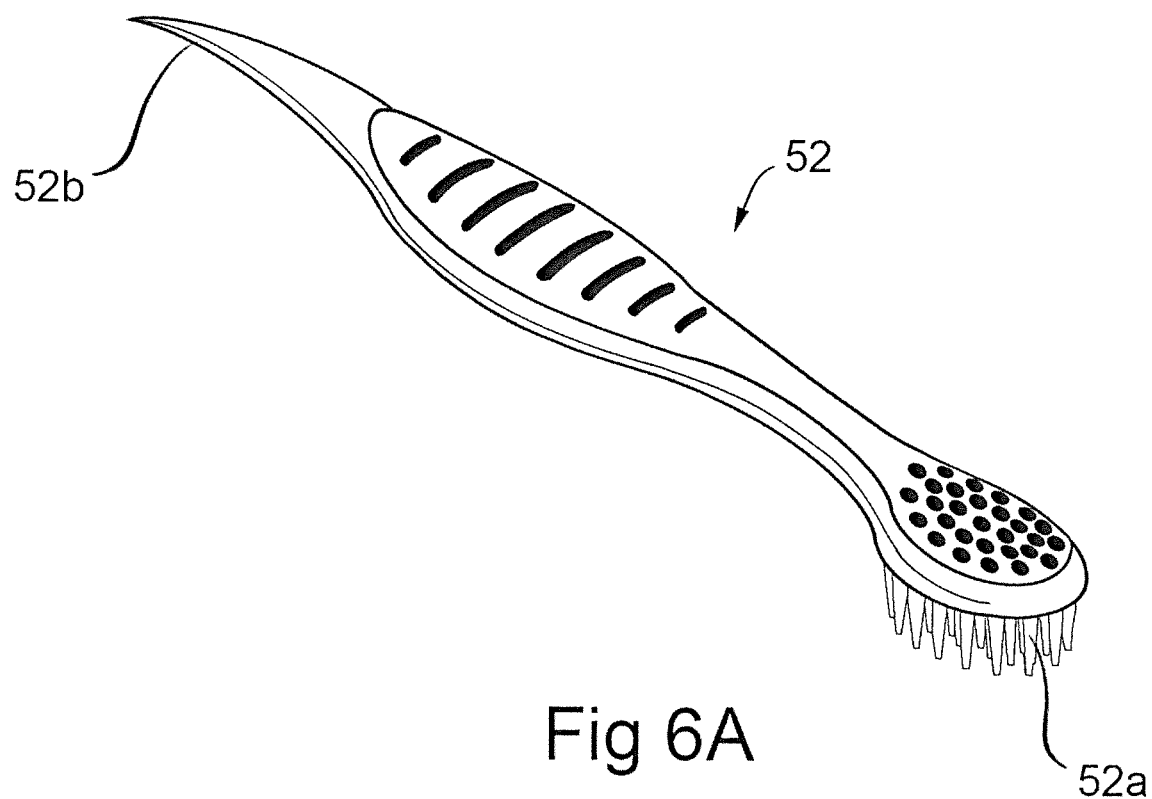
FIG. 6A is a top perspective view of a brush for removing particles or other debris from jewelry to be cleaned, shown with bristles at one end and a tail or pick at the other end.
Figure 6B:
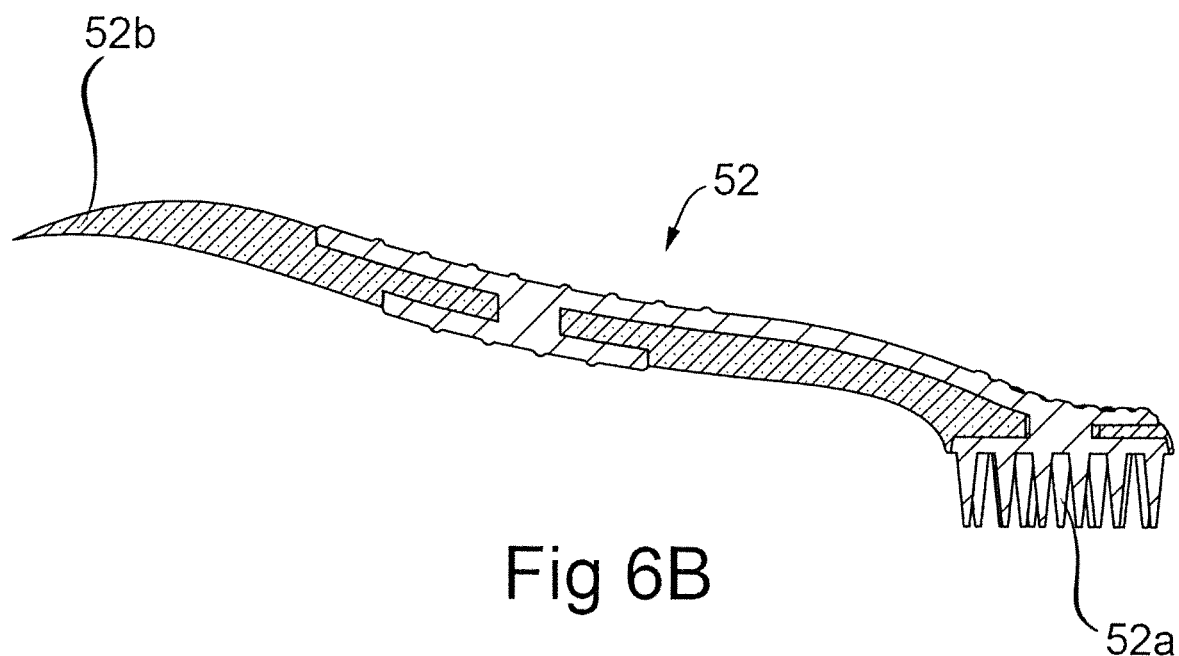
FIG. 6B is a side elevational view, in cross-section of the brush shown in FIG. 6A.

Referring to FIGS. 6A and 6B, a jewelry brush 52, made with Santoprene TPV rubber bristles 52a, has many uses as with any brush except it will not scratch shiny surfaces that are used in most all jewelry finishing. The tail or pick 52b is designed to dig out dirt and grime that has been softened by the cleaning device during the sanitizing step that has hardened and may need some help being removed. The construction of the handle is polypropylene strong also safe to gems and the metals that will be sanitized.

Figure 7:
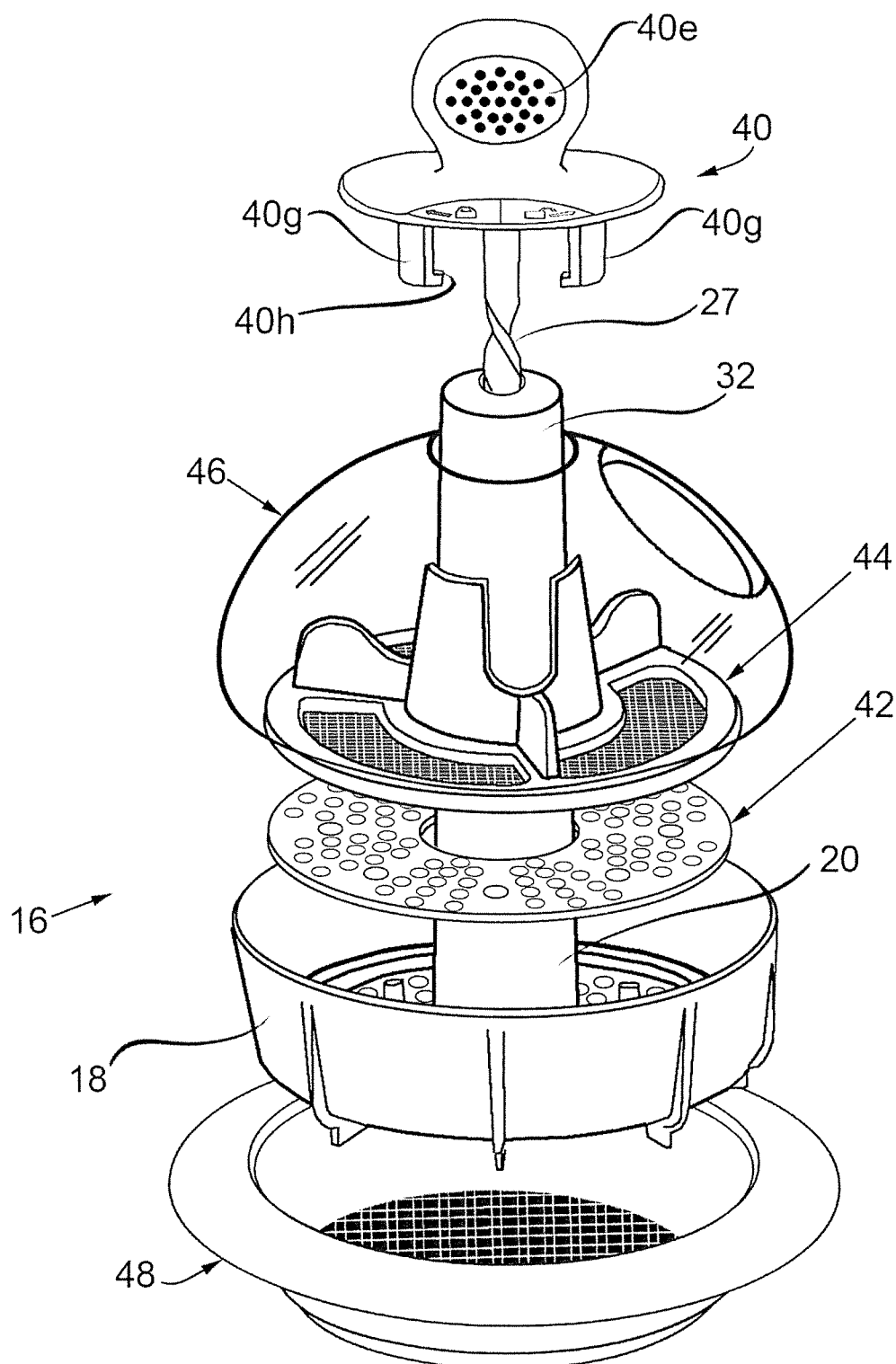
FIG. 7 an exploded view of the spinning mechanism or carousel with a metal disc, a small part stabilizer, a rinse bubble and a plunger assembly positioned over the safety strainer.

FIG. 7 is an exploded view of the spinning mechanism or carousel 16 with a metal disc 42, a small part stabilizer 44, a rinse bubble 46 and a plunger assembly 40 positioned over the safety strainer 48.

Another feature of the invention is to form the outer shell 12b of the jar 12 with a thermochromic material that will change the color of the outer shell in response to attaining a predetermined temperature. The specific thermochromic material used is not critical. However, it should be selected to change light reflection, absorption and/or scattering properties at a predetermined temperature of a liquid heated in the jar 12 placed in a microwave oven (e.g. at 1200 watts) so that the color of the outer shell 12b can be a solid color, such as blue, when the liquid or cleaning solution is at ambient temperature, such as 72° F. After one minute or two minutes, for example, when the temperature reaches approximately 139° F. the outer shell 12b starts to change colors to a light blue with some white regions and after 2-3 minutes when the temperature of the cleaning fluid achieves sanitizing temperature of at least 170° F. the outer surface of the outer shell 12b turns substantially white over the entire visible area. This provides a visual indicator that the fluid or cleaning solution has reached its sanitizing temperature and the container may be removed from the microwave oven and can receive the carousel 16 with the basket 18 and the jewelry or items to be cleaned together with the plunger spinning mechanism for rotating the basket 18 within the heated cleaning fluid.

Figure 8:
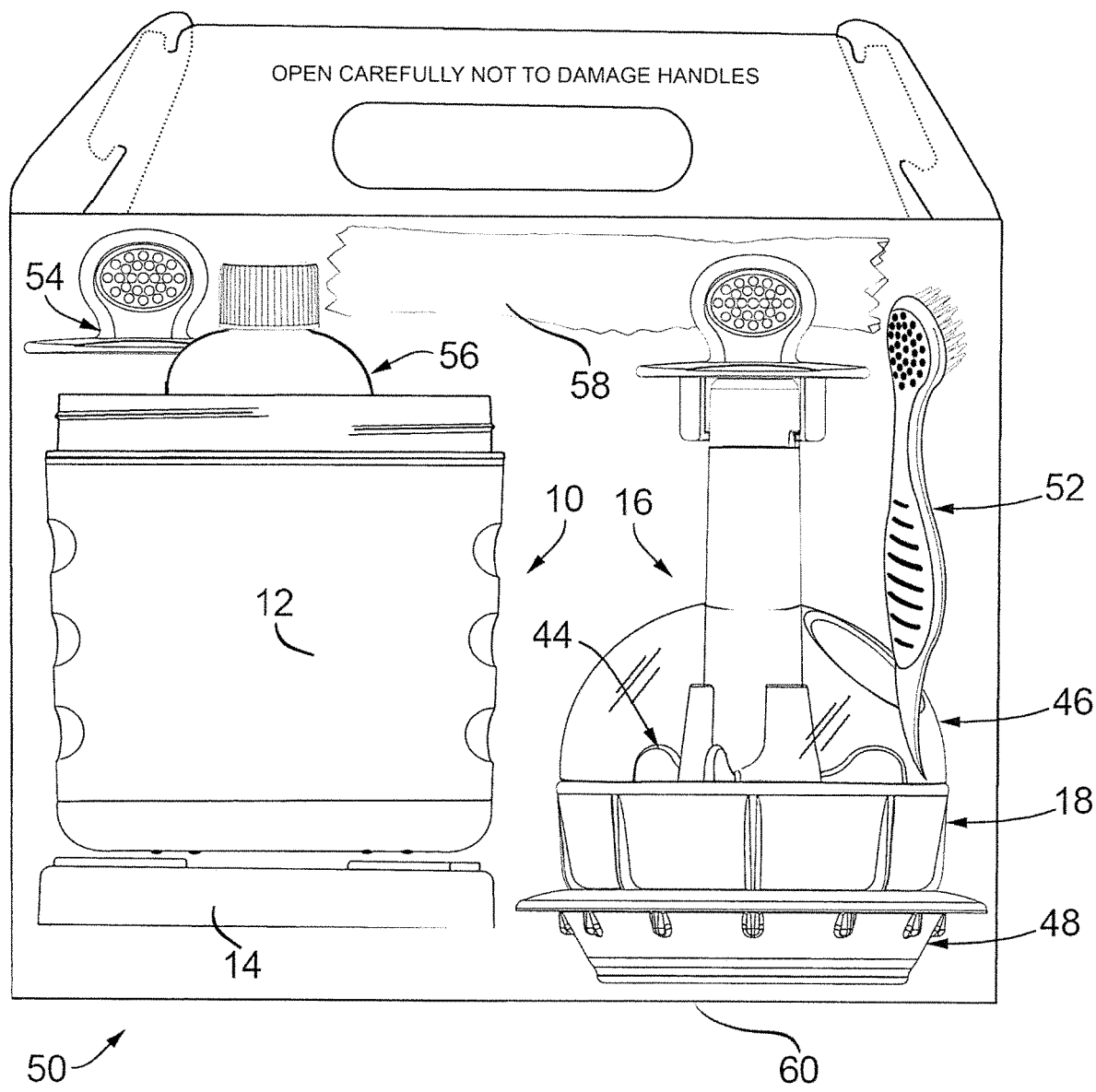
FIG. 8 is a front elevational view of a package or container for all the component parts of a kit forming part of the portable cleaning device.

Referring to FIG. 8, a portable cleaning kit 50 in accordance with the invention includes the following elements or components, some of which may be optional (as noted):
1. A container 10, including a jar 12 and a lid 14;
2. A spinning mechanism or carousel 16, including a basket 18;
3. a metal disc 42;
4. A small parts stabilizer 44;
5. A rinse bubble 46;
6. A safety strainer 48;
7. An optional combination brush and pick 52 (FIGS. 6A and 6B);
8. An optional bottle of cleaning fluid 56;
9. An optional polishing cloth 58;
10. An optional cleaning and resurfacing disc 54; and
11. Package, case or container 60 for housing and storing all the components of the kit.

The use and operation of the device will now be described.
1. The cleaning solution is prepared in accordance with directions of the manufacturer.
2. Fill the jar 12 halfway to top with room temperature tap water.
3. Add recommended amount of cleaning solution.
4. Top off with tap water to the maximum fill line 12f.
5. Place sink safety strainer/caddy 48 over a kitchen sink drain before attempting to use the container. This will allow only water to drain and guard against any parts dropping into the drain.
6. Place the lid counter or caddy 14, top side down, on a kitchen counter next to the sink or other surface where the device will be used.
7. Place the complete spin mechanism or carousel 16 on the lid or on the counter caddy 14. The lid 14 doubles as a work station drip tray for the carousel during operation. The four protruding santoprene rests 14b will grip and keep the basket from spinning thereby allowing the handle 40d to be easily removed or reinstalled to prepare for the Sanitizing or Rinsing steps.
8. The spin handle is designed to be a one handed operation. Remove the handle. With the handle off remove the rinse bubble and small part stabilizer leaving the metal disc 42 in place.
9. Place the rinse bubble 46 and small part stabilizer 44 aside as these will possibly be required during the rinsing step.
10. To remove the handle 40d completely with the jar 12 positioned on the lid or counter caddy 14 to steady it, press handle down then twist the handle counter clockwise (FIG. 9A) to unlock. Then pull straight up and out of the central body or post 20 (FIGS. 9B and 9C).
11. To reinstall the plunger 40 place the lower flat portion 40b of the spiral shaft of the handle into the top of the central body or post 20 and rotate until received through the rectangular slot 30 and let the spiral shaft drop under its own weight. It will drop spinning down into place. Twist counter clockwise until the locking tabs line up and gently push down (FIG. 9D) then twist clockwise to re-engage lock. The basket 18 can be maneuvered with one hand into or out of the jar 12 or during the sanitizing or rinse operation etc.

Figure 9E:
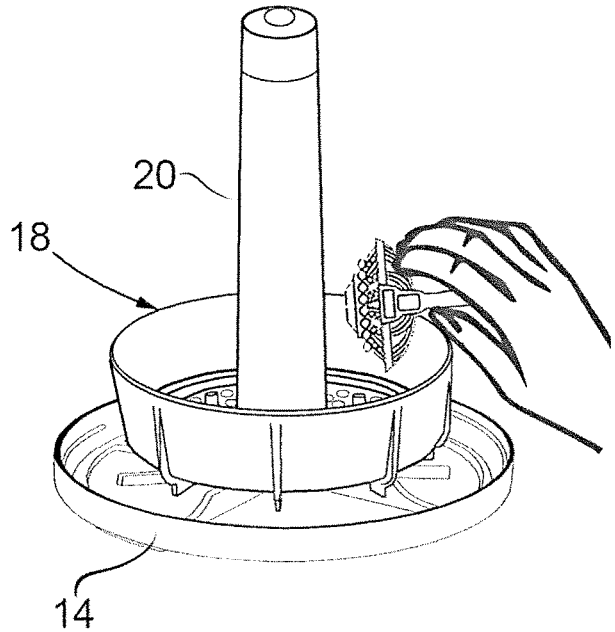
Figure 9F:
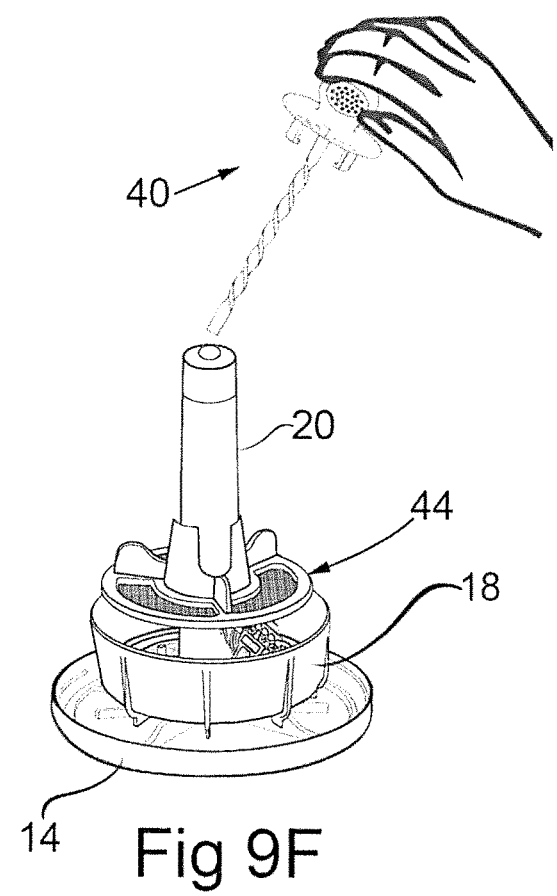
Figure 9G:
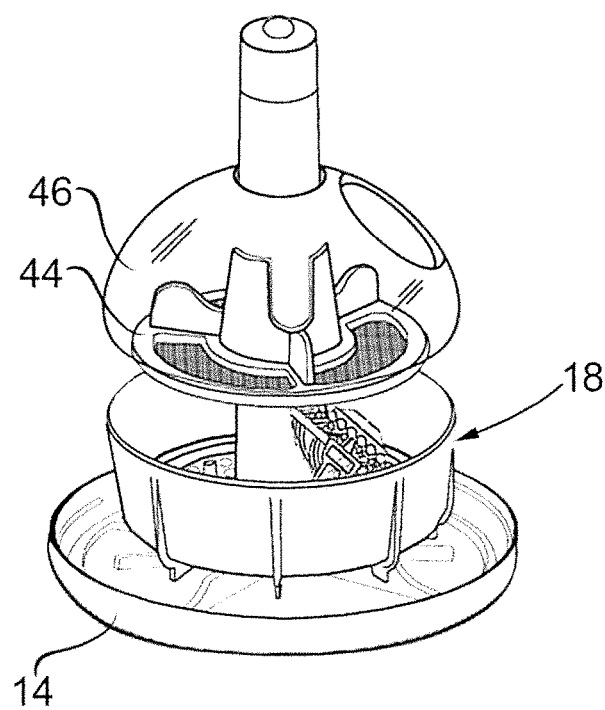
Figure 9H:
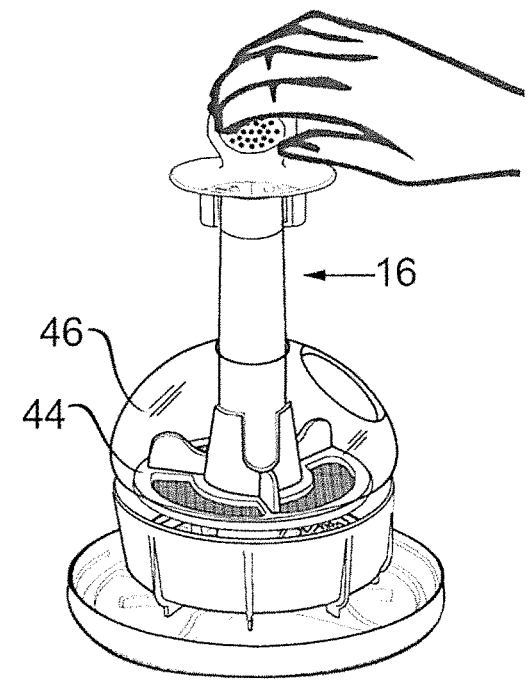

12. Place the item or items to be cleaned and/or Sanitized into the basket 18 lying them on the metal disc 42 (FIG. 9E). Larger heavier items will steady themselves. However, with smaller light weight jewelry like diamond studs, thin chains etc. small part stabilizer 44 can be used at this time (See FIG. 9F). Or both the small parts stabilizer 44 and the rinse bubble 46 can be used for maximum security (FIG. 9G) This will keep the small Jewelry steady while spinning the basket 18 as the items are sanitized or rinsed.
13. Place handle back into the central body or post 20 and lock into lifting position for rinsing, storage etc. (FIG. 9H). The configuration of the device can be tailored for the individual type of jewelry to be cleaned.
14. One item or multiple items can be sanitized according to the types of Jewelry and what can fit in basket.
15. The jar is placed into a microwave oven. The insulating outer sleeve or shell 12b turns white as sanitizing temperature is reached. When sanitizing temperature is reached allow the jar to sit for 30 to 60 seconds then carefully remove the jar and place it on a kitchen counter or other surface where the user will be working.

Heat up time results may vary. The following Table is based on a fresh 12 oz. bath filled to the MAX fill line 12f in the jar 12 at room temperature of 72° F. CAUTION should always be used when heating and removing anything hot from a microwave oven. A safe approach to avoid overheating is to start any of the recommended heating time shown at 1.00 minute 30 seconds and increase in 30 second increments until a sanitizing temperature of 170° F. or higher is reached. See below example color change chart.

TABLE

Jewelry Spa ® HOT TUB ™

| Oven Wattage | Microwave heat up time guide Heat up Time | | Sanitizing Temp ° F. |
|---|---|---|---|
| 700 watts | 3.00 Minutes | 30 Seconds | 170° F. & Up |
| 900 watts | 3.00 Minutes | 15 Seconds | 170° F. & Up |
| 1050 watts | 3.00 Minutes | 0 Seconds | 170° F. & Up |
| 1100 watts | 2.00 Minutes | 45 Seconds | 170° F. & Up |
| 1200 watts | 2.00 Minutes | 0 Seconds | 170° F. & Up |
| 1300 watts | 1.00 Minutes | 30 Seconds | 170° F. & Up |

Figure 9K:
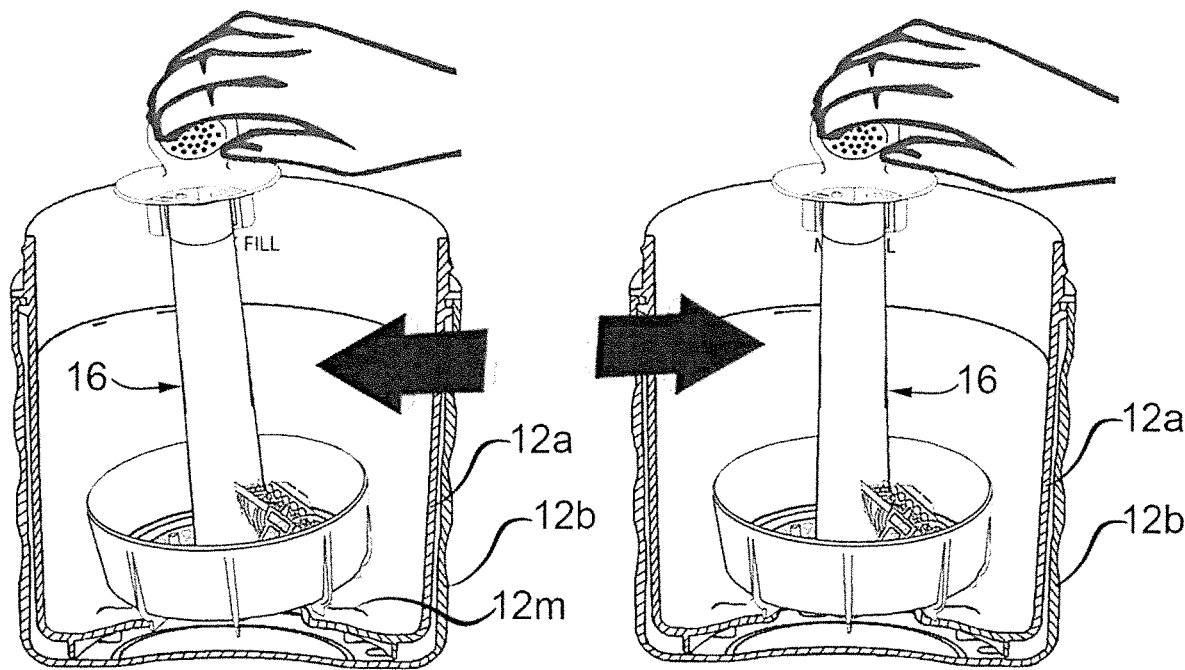
Figure 9K:
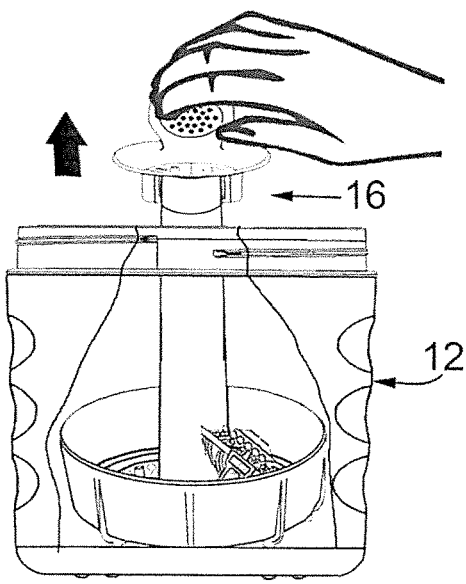
Figure 9L:
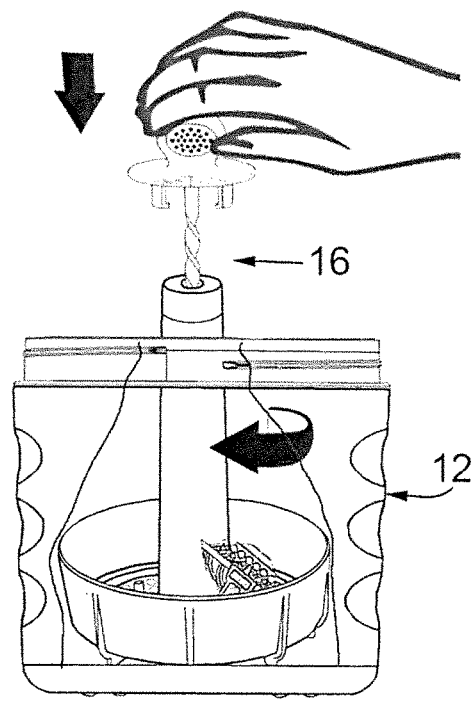

16. The carousel 16 is now ready to be submerged into the jar 12.
17. Using one hand tilt the entire basket towards the side wall of the jar (FIG. 9I). There are stops 12m molded at the bottom of the inner shell 12a that help steady the basket 18 in order to unlock the spin handle 40d. Press down on the handle and pivot to the left to release the spin handle.
18. Once released tilt the basket 18 back to the center along the axis $A_c$ of the jar 12 (FIG. 9J) and pull up handle (FIG. 9K) and then more forcefully push down (FIG. 9L) spinning the basket slowly. Repeat for 30-60 seconds.

When pumping the handle up and down only move the handle halfway so the locking tabs will not hit on the locking cap. The basket can also be allowed to sit and soak for 30-60 seconds. Repeat sanitizing step as necessary.

Figure 9M:
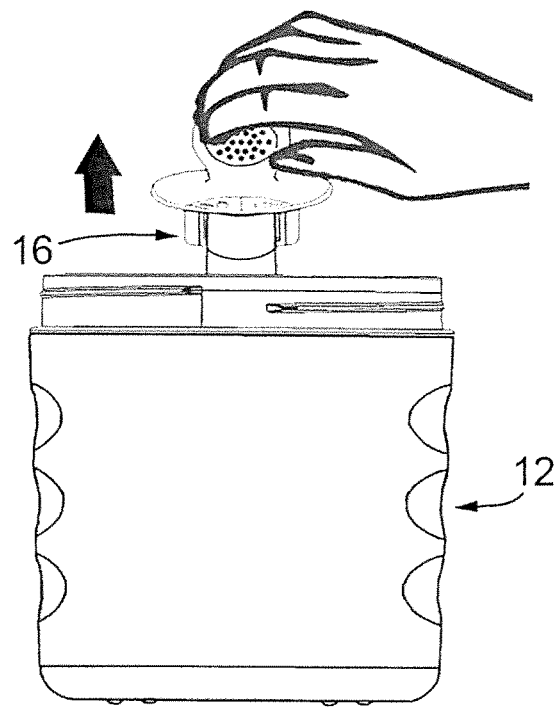
Figure 9N:
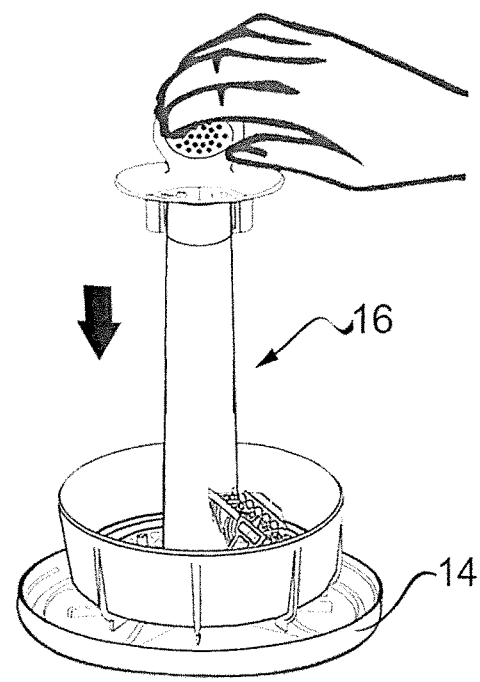
Figure 9O:
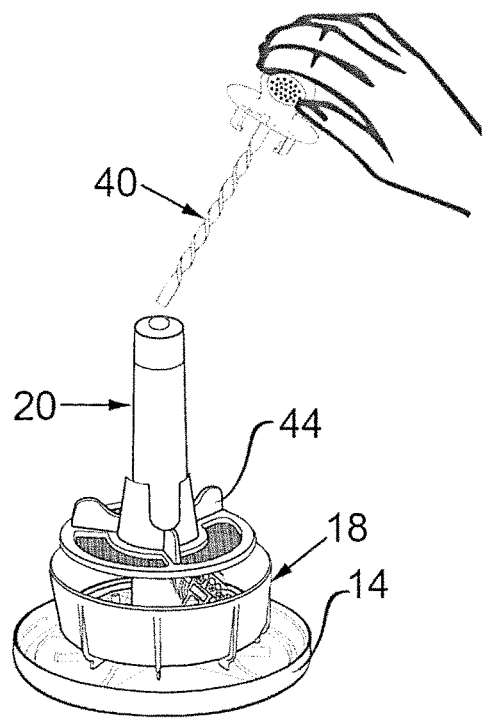
Figure 9P:
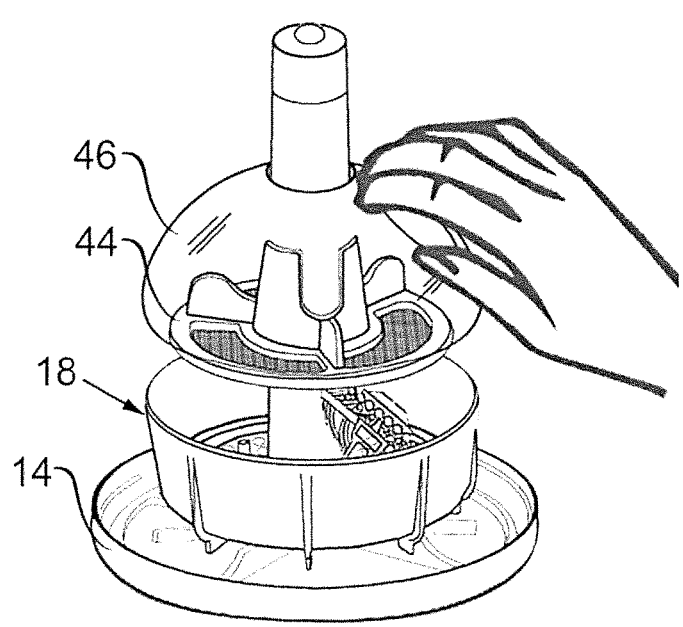
Figure 9Q:
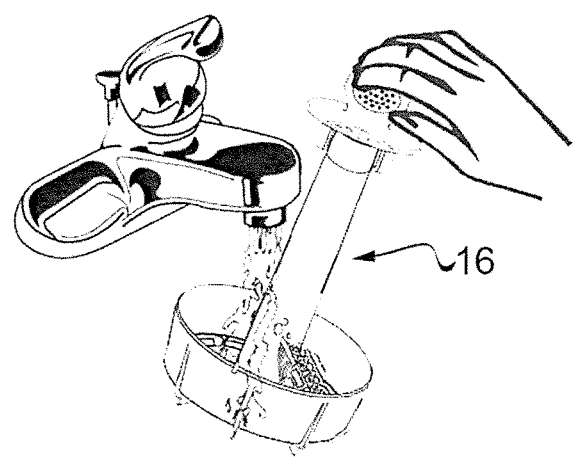
Figure 9R:
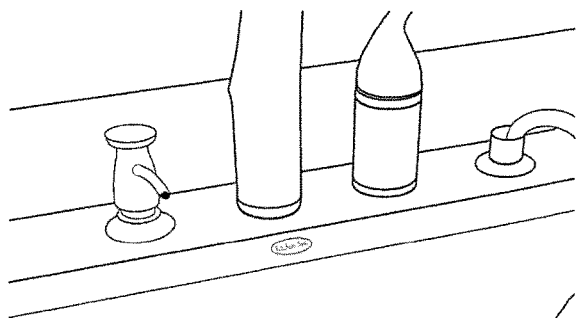
Figure 9R:
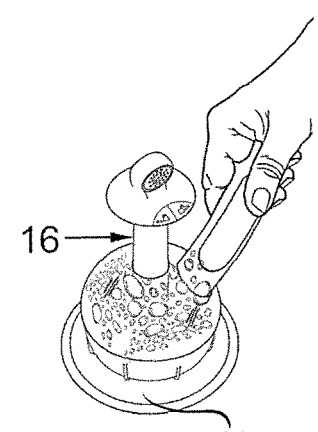
Figure 9S:
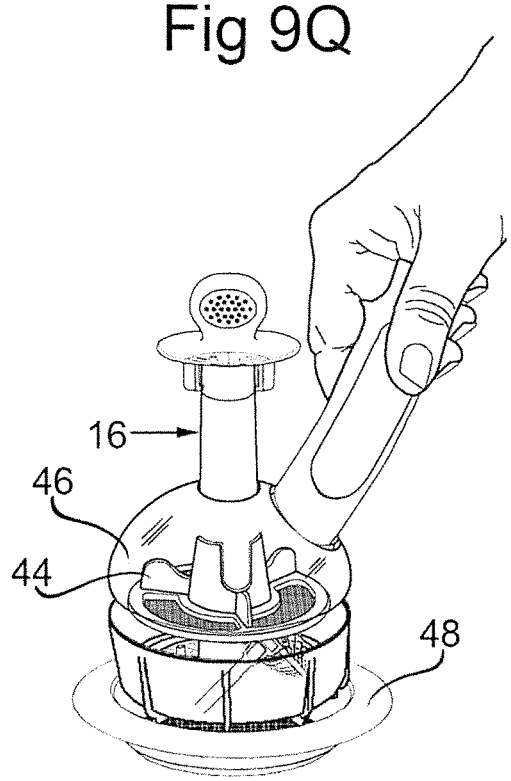
Figure 9T:
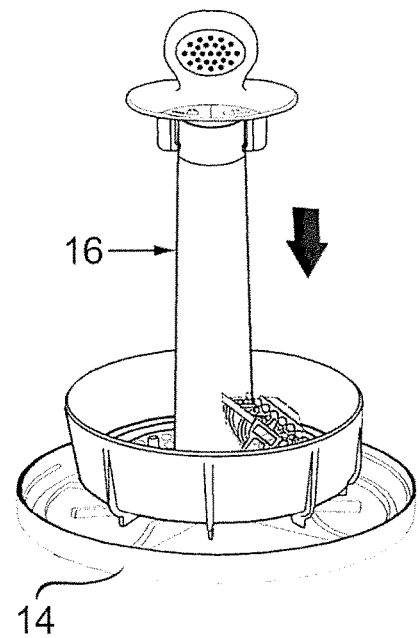
Figure 9U:
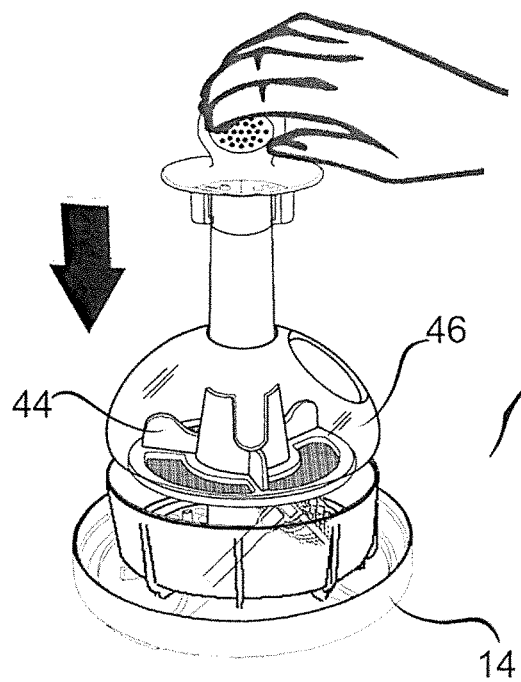
Figure 9V:
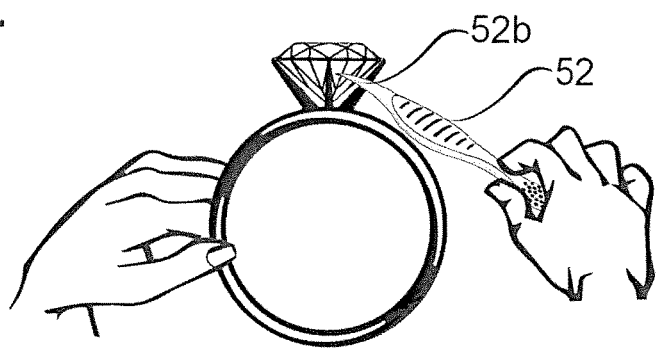
Figure 9W:
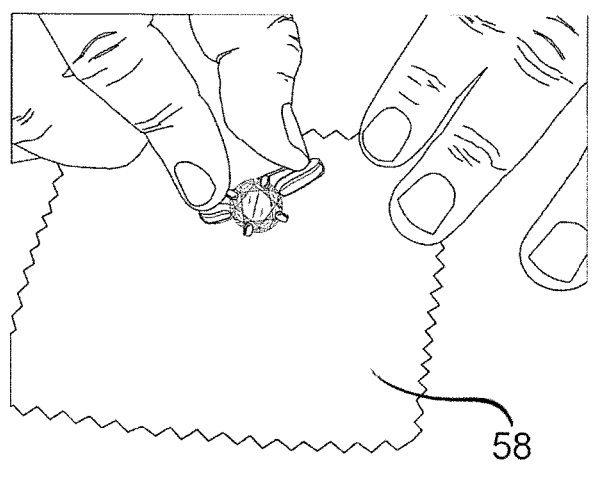
Figure 9X:
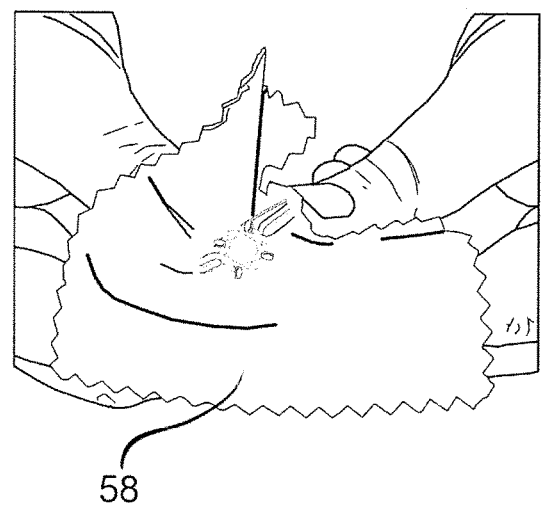
Figure 9Y:
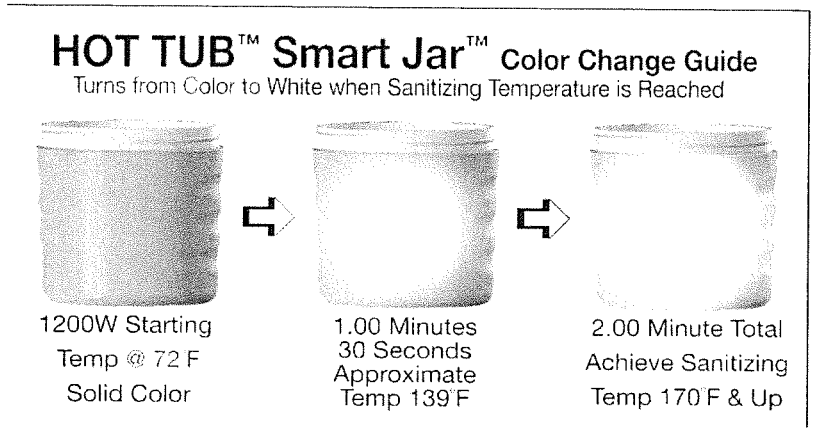

19. To setup for rinse, lock the spin handle 40d in the lifting position (FIG. 9M) and remove the dipping basket 18 out of the jar 12. At this point there are two options for rinsing.
   a) The dipping basket 18 can be placed back onto the lid or counter caddy 14, (FIG. 9N) remove the handle completely, leave the small part stabilizer in place (if used) (FIG. 9O) and place the rinse bubble 46 back into position over the basket 18 (FIG. 9P), replace the handle and lock it in the lifting position then place on the sink safety strainer for rinsing.
   b) The carousel can be removed from the jar 12 and placed on the sink safety strainer caddy 48 for Rinsing (FIG. 9T).
20. Place the carousel onto the sink safety strainer/caddy 48 positioned over the drain earlier. The carousel is designed to sit securely on the strainer caddy. Turn on the faucet to apply hot tap water (jewelry should always be rinsed using hot tap water to avoid thermal shock to gemstones that are known to be prone to this). Now using the sink sprayer position over or directly into the lateral or side opening 46b in the Rinse Bubble 46 and spray the cleaned parts (FIG. 9S). If the sink is not equipped with a sprayer the basket 18 can be held under the faucet spout (FIG. 9Q). For larger jewelry it is not necessary to use the small part stabilizer or the rinse bubble, the jewelry should be heavy enough to stay in place while using either rinsing procedure (FIG. 9R).
21. Place the dipping basket 18 back onto the lid and counter/caddy 14 (FIG. 9T) and allow to cool as rinse water drains. Excess water can also be removed by spinning the basket while sitting on the lid or counter caddy 14 (FIG. 9U). Then the rinse bubble, small part stabilizer can be removed, if used, and finally the jewelry can be removed. The jewelry can be patted dry with a paper towel. If some imbedded grime is still visible the brush/pick 52 (FIG. 9V) can be used to assist, or the above steps can be repeated.
22. The jewelry should always be cleaned in the container 10 before using the polishing cloth 58. Doing so will remove contaminants that may be abrasive and will attach to the polishing cloth. Bypassing the cleaning and rinsing steps will result in scratching the highly polished surface of the jewelry during polishing.
23. The polishing cloth 58 (e.g. the polishing cloth in the kit supplied by Jewelry Spa HOT TUB Inc.) is layed down on a flat surface (FIG. 9W), either side does not matter. Then with smooth even strokes slide the jewelry back and forth. This will help in brightening the high spots on the jewelry where it tends to become dulled by wear.
24. Pick up the jewelry and wrap it in the cloth (FIG. 9X) to get into some of the other areas that may need additional shine. A paper towel can be used to finish wipe.

An approved Testing Laboratory with Good Lab Practices (GLP) tested the device and method and found that the cleaning device 10 is effective in cleaning and/or sanitizing items of jewelry and removing the following representative test organisms: *Staphylococcus aureus, Salmonella* species, *Escherichia coli* and *Pseudomonas*.

Testing was performed by filling the container 10 with approximately 3 ox of room temperature tap water and adding a half bottle (3 oz) solution concentrate. Tap water was added to top off to tub fill line 12f. The container 10 was then placed in a microwave oven. Initially, the microwave oven was set to high for 1 minute 30 seconds and extended by 30 second increments until the sanitizing temperature of 170° F. was achieved. As a visual aid, the tub or container changed color from blue green to white once the proper temperature was reached. The temperature was verified with a thermometer. The heating times/microwave wattage chart was referred to as a guide. Once the proper time was determined for the microwave unit, the same time was used for all subsequent heat ups. After sanitizing temperature was reached, the container or tub was allowed to stabilize in the microwave for an additional 30-60 seconds to avoid potential splash over or spillage.

When exposing the inoculated jewelry to the system of high pH solution and an average temperature of 177° F. for 30 seconds with mechanical agitation, all bacteria present was removed by the process leaving the jewelry bacteria free based on the criteria present in the protocol. When exposing the inoculated jewelry to the system of high pH solution and cold temperature of 76° F. for 30 seconds with mechanical agitation, all bacteria present was also removed by the process leaving the jewelry bacteria free based on the criteria present in the protocol.

On the basis of testing and observations it is clear that the device can be used to clean jewelry and small parts by removing surface contaminants including oils and dirt, sanitizing the surfaces and/or both. Oil, dirt and other surface debris/contaminants can be effectively dislodged and removed by mechanical means including turbulence or agitation of the cleaning fluids in which the jewelry or other parts are immersed and generation of chemical by-products such as generation of gas bubbles in and around the metal disc 42 on which the parts are supported. Heating of the cleaning fluids promotes the process by accelerating chemical reaction release of gases as well as softening surface contaminants that may also harbor embedded pathogens when heated as described the surfaces can also be effectively sanitized.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. A potable cleaning device comprising:
   a generally cylindrical container for receiving a liquid to a predetermined level and defining a container axis and having a bottom wall and a top opening at opposing axial ends along said container axis;
   a basket for supporting items to be cleaned and dimensioned to be removably receivable within said container, said basket defining a basket axis that is substantially coextensive with said container axis when said basket is received within said container and being configured to be rotatably supported for rotation on said bottom wall about said axes when received within said container;
   a metallic disk configured to sit within the basket such that the metallic disk can rotate with the basket, wherein the metallic disk comprises a metal that can be active in oxidation reactions; and
   a spinning means for spinning said basket on said bottom wall about said axes when said basket is received within said container, whereby spinning said basket within said container on said bottom wall when immersed in the liquid below said predetermined level creates turbulence and agitates the liquid while the liquid is in contact with the items to be cleaned to dislodge soil particles and contaminants from the items to be cleaned, and wherein said spinning means is configured to convert linear manual motion of a plunger of the spinning means into rotation of the basket.

2. A cleaning device as defined in claim 1, wherein said basket includes fins for enhancing agitation of the liquid.

3. A cleaning device as defined in claim 1, wherein said basket forms a generally circular tray open in one direction along said basket axis for receiving items to be cleaned and a central boss or projection extending from the circular tray along an opposing direction along said basket axis, said boss or projection being dimensioned to elevate or position said circular tray above said bottom wall of said container when said basket is placed therein, whereby said boss or projection forms an only point of contact between said basket and said bottom wall when said basket is caused to spin by said spinning means.

4. A cleaning device as defined in claim 1, wherein said spinning means comprises a spring.

5. A cleaning device as defined in claim 3, further comprising a stabilizer receivable within said tray for stabilizing the positions of items to be cleaned placed in said tray.

6. A cleaning device comprising:
   a microwavable container for receiving a liquid cleaning solution to a predetermined level and defining a container axis and having a bottom wall and top opening at opposing axis ends along said container axis, wherein said microwavable container can contain the cleaning solution in a microwave oven such that the cleaning solution can be heated in the microwave oven to a temperature in excess of approximately 170° F.;
   a basket for supporting items of jewelry and dimensioned to be removably receivable within said container, said basket defining a basket axis that is substantially coextensive with said container axis when said basket is received within said container and being configured to be rotatably supported for rotation on said bottom wall about said axes when received within said container;
   a metallic disk configured to sit within the basket such that the metallic disk can rotate with the basket, wherein the metallic disk comprises a metal that can be active in oxidation reactions; and
   a spinning means for spinning said basket on said bottom wall about said axes when said basket is received within said container, whereby spinning said basket within said container on said bottom wall when immersed in the cleaning solution below said predetermined level creates turbulence and agitates the cleaning solution in contact with the items of jewelry to dislodge soil particles and contaminants from and sanitize the items of jewelry, and wherein said spinning means is configured to convert linear manual motion of a plunger of the spinning means into rotation of the basket.

7. A cleaning device as defined in claim 6, wherein said basket includes fins for enhancing agitation of the cleaning solution.

8. A cleaning device as defined in claim 6, wherein said basket forms a generally circular tray open in one direction along said basket axis for receiving items to be cleaned and a central boss or projection extending from the circular tray along an opposing direction along said basket axis, said boss or projection being dimensioned to elevate or position said circular tray above said bottom wall of said container when said basket is placed therein, whereby said boss or projection forms an only point of contact between said basket and said bottom wall when said basket is caused to spin by said spinning means.

9. A cleaning device as defined in claim 6, wherein said spinning means comprises a spring.

10. A cleaning device as defined in claim 8, further comprising a stabilizer receivable within said tray for stabilizing the positions of items to be cleaned placed in said tray.

11. A cleaning device as defined in claim 8, further comprising an insulating sleeve substantially enclosing said container to reduce a touch temperature after the cleaning solution is heated in a microwave.

12. A cleaning device as defined in claim 1, wherein said insulating sleeve is dimensioned to create an air space between said container and said insulating sleeve to provide insulation there between.

13. A cleaning device as defined in claim 1, wherein said insulating sleeve is formed of a thermochromic plastic that changes color when a predetermined temperature has been reached.

14. A cleaning device as defined in claim 13, wherein said thermochromic plastic is selected to exhibit a visual color change when the cleaning solution reaches a temperature of at least 170° F.

15. A cleaning device as defined in claim 6, wherein the metallic disk is positionable within the basket such that items to be cleaned may be placed on the metallic disk and in contact with metallic disk, and wherein the metallic disk is capable of being chemically interactive with at least one item to be cleaned and cleaning solution.

16. A cleaning device as defined in claim 6, wherein said metallic disc is formed of aluminum.

17. A cleaning device as defined in claim 15, further comprising a cleaning composition that promotes electrolytic action.

18. A cleaning device as defined in claim 17, wherein said cleaning composition contains sodium carbonate.

19. A portable cleaning kit for cleaning jewelry and small parts, the kit comprising a container for receiving and containing a cleaning liquid; a spinning means having a basket for supporting items to be cleaned and manually operable for spinning the baskets on a bottom wall of the container while the basket supports the items to be cleaned in the cleaning liquid, wherein the spinning means is configured to convert linear manual motion of a plunger of the spinning means into rotation of the basket along an axis that is substantially coextensive with a central axis of the container; and a metal disc receivable within said basket to support the items to be cleaned, wherein the metal disc comprises a metal that can be active in oxidation reactions.

20. A kit as defined in claim 19, the kit further comprising a small parts stabilizer for securing items to be cleaned while said basket is rotated.

21. A kit as defined in claim 19, the kit further comprising a dome-shaped rinse bubble for covering the items to be cleaned after they have been cleaned and having an opening therein for directing a stream or spray of water to remove cleaning solution from said items.

22. A kit as defined in claim 19, the kit further comprising a safety strainer for placement over a drain in order to prevent cleaned parts from dropping into the drain.

23. A kit as defined in claim 19, the kit further comprising a polishing cloth.

24. A kit as defined in claim 19, the kit further comprising a brush and pick implement.

25. A kit as defined in claim 19, the kit further comprising a resurfacing disc.

26. A kit as defined in claim 19, the kit further comprising a packaging container for receiving kit components.

27. A kit as defined in claim 19, the kit further comprising a cleaning solution.

28. A kit as defined in claim 19, the kit further comprising:
a small parts stabilizer; a dome-shaped rinse bubble; a safety strainer; a polishing cloth;
a brush and pick implement; a resurfacing disc; a packaging container and a cleaning solution.

* * * * *